(12) United States Patent
Keusenkothen et al.

(10) Patent No.: US 9,988,325 B2
(45) Date of Patent: Jun. 5, 2018

(54) HYDROCARBON CONVERSION

(71) Applicant: ExxonMobil Chemical Patents Inc., Baytown, TX (US)

(72) Inventors: Paul F. Keusenkothen, Houston, TX (US); John S. Buchanan, Flemington, NJ (US); Samia Ilias, Somerville, NJ (US); Mayank Shekhar, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days. days.

(21) Appl. No.: 15/240,562

(22) Filed: Aug. 18, 2016

(65) Prior Publication Data
US 2017/0088492 A1   Mar. 30, 2017

Related U.S. Application Data

(60) Provisional application No. 62/232,609, filed on Sep. 25, 2015, provisional application No. 62/234,262, filed on Sep. 29, 2015.

(30) Foreign Application Priority Data

Nov. 19, 2015 (EP) ..................................... 15195311
Nov. 19, 2015 (EP) ..................................... 15195314

(51) Int. Cl.
*C07C 2/76* (2006.01)
*C07C 5/41* (2006.01)

(52) U.S. Cl.
CPC ................ *C07C 5/415* (2013.01); *C07C 2/76* (2013.01); *C07C 2529/06* (2013.01)

(58) Field of Classification Search
None
See application file for complete search history.

(56) References Cited

U.S. PATENT DOCUMENTS

| | | |
|---|---|---|
| 3,702,886 A | 11/1972 | Argauer et al. |
| 3,709,979 A | 1/1973 | Chu et al. |
| 3,832,449 A | 8/1974 | Rosinski et al. |
| 3,960,978 A | 6/1976 | Givens et al. |
| 4,016,245 A | 4/1977 | Plank et al. |
| 4,021,502 A | 5/1977 | Plank et al. |
| 4,076,842 A | 2/1978 | Plank et al. |
| RE29,948 E | 3/1979 | Dwyer et al. |
| 4,150,062 A | 4/1979 | Garwood et al. |
| 4,227,992 A | 10/1980 | Garwood et al. |
| 4,229,424 A | 10/1980 | Kokotailo |
| 4,234,231 A | 11/1980 | Yan |

(Continued)

FOREIGN PATENT DOCUMENTS

| | | |
|---|---|---|
| EP | 293032 | 5/1988 |
| WO | 97/17290 | 5/1997 |

(Continued)

*Primary Examiner* — Tam M Nguyen

(57) ABSTRACT

The invention relates to the hydrocarbon upgrading to produce aromatic hydrocarbon, to equipment and materials useful in such upgrading, and to the use of such upgrading for, e.g., producing aromatic hydrocarbon natural gas. The upgrading can be carried out in the presence of a dehydrocyclization catalyst comprising at least one dehydrogenation component and at least one molecular sieve.

25 Claims, 2 Drawing Sheets

(56) References Cited

U.S. PATENT DOCUMENTS

| | | | |
|---|---|---|---|
| 4,439,409 A | 3/1984 | Puppe et al. | |
| 4,456,781 A | 6/1984 | Marsh et al. | |
| 4,556,477 A | 12/1985 | Dwyer | |
| 4,826,667 A | 5/1989 | Zones et al. | |
| 4,855,522 A | 8/1989 | Diaz | |
| 4,954,325 A | 9/1990 | Rubin et al. | |
| 5,026,937 A | 6/1991 | Bricker | |
| 5,236,575 A | 8/1993 | Bennett et al. | |
| 5,250,277 A | 10/1993 | Kresge et al. | |
| 5,362,697 A | 11/1994 | Fung et al. | |
| 5,633,417 A | 5/1997 | Beck et al. | |
| 5,675,047 A | 10/1997 | Beck et al. | |
| 6,077,498 A | 6/2000 | Diaz Cabanas et al. | |
| 6,670,517 B1 | 12/2003 | Abichandani et al. | |
| 7,186,871 B2 | 3/2007 | Mitchell et al. | |
| 7,186,872 B2* | 3/2007 | Juttu | B01J 29/87 585/418 |
| 7,728,186 B2* | 6/2010 | Iaccino | C07C 2/76 585/407 |
| 8,692,043 B2 | 4/2014 | Lauritzen et al. | |
| 8,835,706 B2* | 9/2014 | Iyer | C07C 2/76 585/301 |
| 9,732,013 B2* | 8/2017 | Buchanan | C07C 1/20 |
| 2008/0249342 A1* | 10/2008 | Iaccino | B01J 29/48 585/402 |
| 2009/0209794 A1 | 8/2009 | Lauritzen et al. | |
| 2011/0251444 A1 | 10/2011 | Jois et al. | |
| 2012/0240467 A1 | 9/2012 | Iyer et al. | |
| 2016/0122256 A1* | 5/2016 | Wang | C07C 4/18 585/315 |
| 2016/0237002 A1* | 8/2016 | Vestre | B01J 19/2475 |
| 2017/0007992 A1* | 1/2017 | Lishchiner | B01J 29/061 |
| 2017/0088486 A1* | 3/2017 | Buchanan | C07C 2/76 |
| 2017/0088490 A1* | 3/2017 | Chen | C07C 5/3335 |

FOREIGN PATENT DOCUMENTS

| | | |
|---|---|---|
| WO | 2010/140005 | 12/2010 |
| WO | 2012/078506 | 6/2012 |

* cited by examiner

HYDROCARBON CONVERSION

CROSS-REFERENCE TO RELATED APPLICATIONS

This invention claims priority to and the benefit of U.S. Patent Application Ser. No. 62/232,609 filed Sep. 25, 2015, and 62/234,262, filed Sep. 29, 2016; and European Patent Application Nos. 15195311.4 filed Nov. 19, 2015, and 15195314.8 filed Nov. 19, 2015, all of which are incorporated by reference in their entireties. The following related cases are also incorporated by reference in their entireties: U.S. Patent Application Ser. No. 62/234,240; European Patent Application No. 15197698.2; U.S. Patent Application Ser. No. 62/247,795; European Patent Application No. 15197700.6; U.S. Patent Application Ser. No. 62/248,374; European Patent Application No. 15197702.2; U.S. Patent Application Ser. No. 62/253,268; U.S. Patent Application Ser. No. 62/298,655; European Patent Application No. 16167672.1; U.S. Patent Application Ser. No. 62/326,918; European Patent Application No. 16175163.1; U.S. Patent Application Ser. No. 62/299,730; European Patent Application No. 16167395.9; U.S. Patent Application Ser. No. 62/313,288; European Patent Application No. 16173587.3; U.S. Patent Application Ser. No. 62/313,306, and European Patent Application No. 16173980.0.

FIELD

The invention relates to upgrading hydrocarbon to higher-value hydrocarbon such as aromatic hydrocarbon, to equipment and materials useful in such upgrading, and to the use of such upgrading for, e.g., the conversion of natural gas to aromatic hydrocarbon.

BACKGROUND

Aromatic hydrocarbon compounds such as benzene are frequently used for producing transportation fuels and petrochemicals such as styrene, phenol, nylon and polyurethanes and many others. Benzene is typically produced in processes such a steam cracking and catalytic reforming. During steam cracking, a $C_{2+}$ hydrocarbon feed is exposed to high-temperature pyrolysis conditions to produce a product comprising molecular hydrogen, $C_{4-}$ olefin, other $C_{4-}$ hydrocarbon, and $C_{5+}$ hydrocarbon. The yield of aromatic hydrocarbon from steam cracking is generally much less than the yield of light hydrocarbon. Consequently, complex processes typically are needed for separating and recovering aromatic hydrocarbon from steam cracker effluent. Catalytic naphtha reforming produces a product having a much greater content of aromatic hydrocarbon than steam cracker effluent, but the naphtha feed is itself useful for other purposes such as a motor gasoline blendstock.

Various attempts have been made to overcome these difficulties, and provide an efficient process for producing aromatic hydrocarbon at high yield from a relatively inexpensive feed. For example, processes have been developed for producing light aromatic hydrocarbon (e.g., benzene, toluene, and xylenes—"BTX") from paraffinic $C_{4-}$ feeds. The processes typically utilize an acidic molecular sieve such as ZSM-5 and at least one metal having dehydrogenation functionality, such as one or more of Pt, Ga, Zn, and Mo. These conventional processes typically operate at high temperature and low pressure. Although these conditions are desirable for producing aromatic hydrocarbon, they also lead to undue catalyst deactivation as a result of increased catalyst coking. Catalyst coking generally worsens under conditions which increase feed conversion, leading to additional operating difficulties.

One way to lessen the amount of catalyst coking is disclosed in U.S. Pat. No. 5,026,937. The reference discloses removing $C_{2+}$ hydrocarbon from the feed in order to increase the feed's methane concentration. Since ethane, propane, and butanes are less refractory, removing these compounds from the feed decreases the amount of over-cracking, and lessens the accumulation of catalyst coke. The process utilizes a catalyst comprising molecular sieve, an amorphous phosphorous-modified alumina, and at least one dehydrogenation metal selected from Ga, Pt, Rh, Ru, and Ir. The catalyst contains ≤0.1 wt. % of Ni, Fe, Co, Group VIb metals, and Group VIIb metals. The reference also discloses increasing aromatic hydrocarbon yield by removing hydrogen from the reaction, e.g., by combusting the hydrogen with oxygen in the presence of an oxidation catalyst that has greater selectivity for hydrogen combustion over methane combustion.

Processes have also been developed for converting less-refractory paraffinic hydrocarbon to aromatic hydrocarbon with decreased selectivity for catalyst coke. For example, U.S. Pat. No. 4,855,522 discloses converting $C_2$, $C_3$, and $C_4$ hydrocarbon with increased selectivity for aromatic hydrocarbon and decreased selectivity for catalyst coke. The process utilizes a dehydrocyclization catalyst comprising (a) an aluminosilicate having a silica:alumina molar ratio of at least 5 and (b) a compound of (i) Ga and (ii) at least one rare earth metal. The reference discloses carrying out the aromatization conversion at a space velocity (LHSV) in the range of from 0.5 to 8 hr$^{-1}$, a temperature ≥450° C. (e.g., 475° C. to 650° C.), a pressure of from 1 bar to 20 bar, and a feed contact time of 1 to 50 seconds.

More recently, Catalysts have been developed to further reduce the amount of catalyst coking during the dehydrocyclization of $C_{4-}$ paraffinic hydrocarbon. For example, increasing the catalyst's dehydrogenation metal loading has been observed to lessen the amount of catalyst coking. See, e.g., U.S. Pat. No. 7,186,871. But increasing dehydrogenation metal loading has been found to increase the catalyst's hydrogenolysis activity, resulting in an increase in the amount of methane and other light saturated hydrocarbon in the reaction product and a decrease in the amount of the desired aromatic hydrocarbon. This effect can be mitigated by further increasing catalyst complexity, e.g., by adding an attenuating metal to the catalyst as disclosed in U.S. Pat. No. 8,692,043.

Hydrogenolysis side-reactions can also be mitigated by carrying out the aromatization in two stages. For example, U.S. Pat. No. 8,835,706 discloses aromatization of an ethane-propane feed. The feed is obtained from natural gas by cryogenically separating methane. The feed is reacted in a first stage operated under conditions which maximize the conversion of propane to aromatics. Following separation of the aromatic hydrocarbon, ethane and any other non-aromatic hydrocarbon produced in the first stage are converted to aromatics in a second stage. The second stage is operated under conditions which maximize the conversion of ethane to aromatic hydrocarbon. Two fixed-bed reactors can be used in each stage. The process can be operated continuously by cycling between the first and second reactor in each stage, with the first reactor carrying out aromatization while the second reactor undergoes decoking, and vice versa. The patent discloses that increased catalyst coking can be overcome by utilizing fluidized catalyst beds in the reaction stages. Decreasing the amount of time (the "cycle time") that a fixed bed reactor is operated in aromatization mode before switching to decoking mode can also be used to lessen the amount of coke accumulation.

Improved processes are needed for dehydrocyclization of light paraffinic hydrocarbon that exhibit one or more of a greater feed conversion, a greater yield of aromatic hydrocarbon, and a lesser yield of undesired byproducts such as catalyst coke and $C_{4-}$ hydrocarbon. Processes are particularly desired which can be carried out with catalysts of lesser complexity, in fixed catalyst beds with increased cycle time, and/or without the need for cryogenic separation.

SUMMARY

The invention relates to a hydrocarbon conversion process carried out in at least three stages. The feed to the process comprises substantially non-aromatic hydrocarbon. At least a portion of the feed's non-aromatic hydrocarbon is reacted in a first stage under dehydrocyclization conditions to produce a first product comprising aromatic hydrocarbon and molecular hydrogen. A second stage is provided for removing at least a portion of the first product's aromatic hydrocarbon to produce a raffinate having a lesser aromatic hydrocarbon content. The raffinate is reacted in a third stage in the presence of a second catalyst under dehydrocyclization conditions to produce a second product comprising additional aromatic hydrocarbon and additional molecular hydrogen. It has been discovered that operating the first stage at a lesser temperature and greater pressure than the third stage, results in improvements over conventional processes including a greater selectivity to the desired aromatic hydrocarbon and a lesser selectivity to catalyst coke.

Accordingly, certain aspects of the invention relate to a hydrocarbon conversion process. The feed to the process comprises $A_1$ wt. % ethane, wherein $A_1 \geq 1$. The process includes contacting the feed with a first catalyst which comprises $\geq 10$ wt. % of a first molecular sieve component and $\geq 0.005$ wt. % of a first dehydrogenation component. The contacting is carried out under catalytic dehydrocyclization conditions which include a temperature $T_1$ in the range of from 400° C. to 630° C. and a pressure $P_1$. Contacting the feed with the first catalyst under these conditions produces a first product comprising (i) $\geq 1$ wt. % aromatic hydrocarbon, (ii) molecular hydrogen, (iii) $A_2$ wt. % ethane, wherein $A_2 \geq 0.75 \cdot A_1$. A raffinate is produced from the first product by removing an extract comprising $\geq 50$ wt. % of the first product's aromatic hydrocarbon, wherein (i) the raffinate comprises $A_3$ wt. % ethane and (ii) $A_3 > A_2$. The process further includes contacting at least a portion of the raffinate with a second catalyst which comprises $\geq 10$ wt. % of a second molecular sieve component and $\geq 0.005$ wt. % of a second dehydrogenation component. This is carried out under catalytic dehydrocyclization conditions, including a temperature $T_2$ in the range of from 450° C. to 700° C. and a pressure $P_2 \leq 35$ psia (241.3 kPa), wherein $T_1 \leq 0.90 \cdot T_2$ and $P_2 < P_1$. Contacting the raffinate with the second catalyst under these conditions produces a second product comprising $\geq 0.5$ wt. % of additional aromatic hydrocarbon and an amount $A_4$ wt. % of ethane, wherein $A_4 < A_3$, and $(A_4/A_3) < (A_2/A_1)$.

In other aspects, the invention relates to a hydrocarbon upgrading process. The feed to the process comprises $A_1$ wt. % ethane, wherein $A_1 \geq 10$, 1 wt. % to 40 wt. % butanes, 20 wt. % to 50 wt. % propane, and 20 to 50 wt. % butanes. The process includes contacting the feed with the specified first catalyst under the specified catalytic dehydrocyclization conditions. Contacting the feed with the first catalyst under these conditions produces a first product comprising $\geq 10$ wt. % aromatic hydrocarbon; molecular hydrogen; $A_2$ wt. % ethane, wherein $A_2 \geq A_1$; 1 wt. % to 40 wt. % methane; $\leq 1$ wt. % propane; and $\leq 1$ wt. % butanes. A raffinate is produced from the first product by removing an extract comprising $\geq 90$ wt. % of the first product's aromatic hydrocarbon. The raffinate comprises $A_3$ wt. % ethane, with $A_3 \geq 1.25 \cdot A_2$. The process further includes contacting at least a portion of the raffinate with the specified second catalyst under the specified catalytic dehydrocyclization conditions to produce a second product comprising $\geq 0.5$ wt. % of additional aromatic hydrocarbon and $A_4$ wt. % of ethane, wherein $A_4 \leq 0.95 \cdot A_3$ and $(A_4/A_3) \leq 0.95 \cdot (A_2/A_1)$.

Although the invention is compatible with feeds comprising ethane, ethane is not a required feed component. In other aspects, the invention relates to a process for upgrading paraffinic hydrocarbon, such as a feed comprising $A_1$ wt. % ethane, $\leq 1$ wt. % of aromatic hydrocarbon, and $\geq 1$ wt. % of $C_{3+}$ paraffinic hydrocarbon, wherein $A_1 < 1$. The process includes contacting the feed with the specified first catalyst under the specified catalytic dehydrocyclization conditions to produce a first product comprising $\geq 10$ wt. % aromatic hydrocarbon, molecular hydrogen, $A_2$ wt. % ethane, 1 wt. % to 40 wt. % methane, $\leq 2$ wt. % propane, and $\leq 1$ wt. % butanes, wherein $A_2 \geq 1$ wt. %. A raffinate is produced by removing from the first product an extract comprising $\geq 90$ wt. % of the first product's aromatic hydrocarbon. The raffinate comprises $A_3$ wt. % ethane, with $A_3 \geq 1.25 \cdot A_2$. The process further includes contacting at least a portion of the raffinate with the specified second catalyst under the specified catalytic dehydrocyclization conditions to produce a second product comprising $\geq 1$ wt. % of additional aromatic hydrocarbon and an amount $A_4$ wt. % of ethane; wherein $A_4 \leq 0.95 \cdot A_3$.

Other aspects relate to a natural gas upgrading process. In these aspects, the feed includes natural gas, e.g., natural gas comprising methane and $\geq 13$ wt. % ethane. The process includes contacting the feed with the specified first catalyst under the specified catalytic dehydrocyclization conditions to produce a first product comprising $\geq 10$ wt. % aromatic hydrocarbon; molecular hydrogen; $A_2$ wt. % ethane, wherein $A_2 \geq A_1$; methane; $\leq 2$ wt. % propane; and $\leq 1$ wt. % butanes. A raffinate is produced by removing from the first product an extract comprising $\geq 90$ wt. % of the first product's aromatic hydrocarbon. The raffinate comprises $A_3$ wt. % ethane, with $A_3 \geq 1.25 \cdot A_2$, $\geq 95$ wt. % of the first product's molecular hydrogen, and $\geq 95$ wt. % of the first product's methane. The process includes contacting the raffinate with the specified second catalyst under catalytic dehydrocyclization conditions which include a temperature $T_2$ in the range of from 450° C. to 700° C. and a pressure $P_2 \leq 35$ psia (241.3 kPa), with $T_1 \leq 0.90 \cdot T_2$ and $P_2 \leq 0.90 \cdot P_1$. The catalytic dehydrocyclization conditions encompass a maximum ethane conversion to aromatic hydrocarbon $X_{ME}$. Contacting the raffinate with the second catalyst converts the raffinate's ethane to aromatic hydrocarbon at a conversion $X_3$, with $X_3 \leq 0.90 \cdot X_{ME}$. Contacting the raffinate with the second catalyst under these conditions produces a second product comprising $\geq 2$ wt. % of additional aromatic hydrocarbon and an amount $A_4$ wt. % of ethane; wherein $A_4 \leq 0.95 \cdot A_3$ and $(A_4/A_3) \leq 0.95 \cdot (A_2/A_1)$. The process further includes producing a second raffinate by removing from the second product an extract comprising $\geq 90$ wt. % of any of the aromatic hydrocarbon in the second product and $\geq 90$ wt. % of the additional aromatic hydrocarbon. The second raffinate comprises $\leq 12$ wt. % ethane, $\leq 5$ wt. % propane, $\leq 2$ wt. % butanes, and $\geq 95$ wt. % the balance of the raffinate comprises methane. The second raffinate has a Wobbe Index in the range of from 49.01 MJ/sm$^3$ to 52.22 MJ/sm$^3$ and has heating value in the range of from 36.07 MJ/sm$^3$ to 41.40 MJ/sm$^3$. The process can include cryogenic methane separation, but this is not required.

Other aspects of the invention include systems apparatus, and catalysts for carrying out any of the proceeding processes.

DETAILED DESCRIPTION

Figure 1:
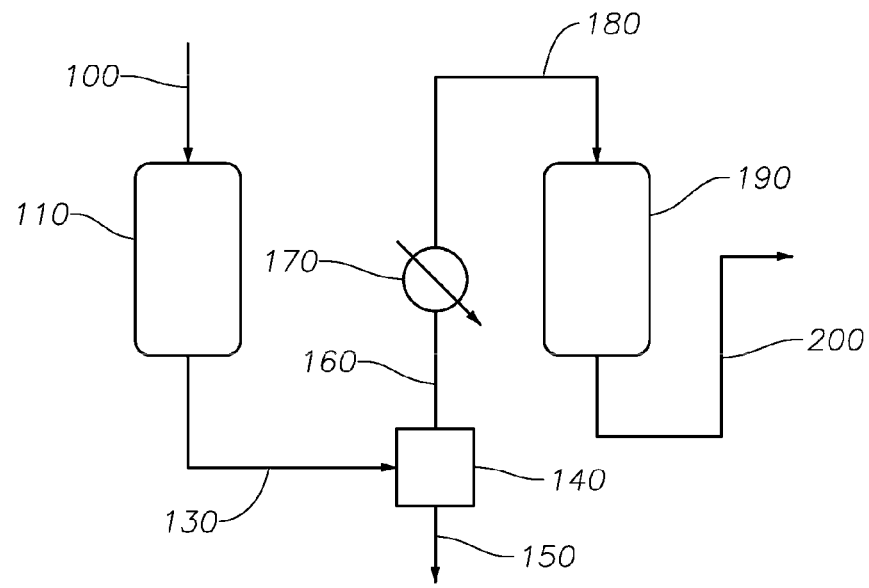
FIG. 1 schematically illustrates certain aspects of the invention which include at least three stages.

It has been found that when operating the first and third stages under the specified temperature and pressure conditions, removing at least a portion of the first product's aromatic hydrocarbon leads to (i) an increased conversion of the remainder of the first product (the raffinate) to aromatic hydrocarbon, (ii) a greater than expected selectivity for the desired aromatic hydrocarbon, and less than the expected selectivity for catalyst coke, even though the third stage is operated at a higher temperature than the first stage. Advantageously, more aromatic hydrocarbon is produced at greater run lengths without catalyst regeneration (e.g., greater cycle time) compared with conventional processes converting substantially the same feed. Unexpectedly, the process has also been found to be less selective for undesirable light hydrocarbon byproducts compared to conventional processes. Even though it is operated at a lesser temperature, typically some $C_2$ hydrocarbon is produced in the first stage, e.g., by hydrogenolysis of $C_{3+}$ hydrocarbon that may be present in the feed. While not wishing to be bound by any theory or model, it is believed that (i) operating the third stage at a greater temperature but lesser pressure and (ii) with a raffinate feed that is richer in $C_2$ hydrocarbon and leaner in aromatic hydrocarbon than the first product, increases the selectivity of the raffinate's light hydrocarbon (particularly the raffinate's ethane) to the desired aromatic hydrocarbon.

It has also been found that these advantages accrue irrespective of the feed's $C_2$ hydrocarbon content. For example, reacting a light hydrocarbon feeds containing <1 wt. % ethane in the first stage under the specified conditions typically results in conversion of at least a portion of the feed to ethane. This in turn typically leads to the presence of ethane in the raffinate. The third stage uses a greater reaction temperature than does the first stage, resulting in the selective conversion of at least a portion of the raffinate's ethane to aromatic hydrocarbon. When the feed contains 1 wt. % to 100 wt. % ethane, utilizing the specified conditions in stages 1, 2, and 3 has been found to increase feed ethane selectivity to aromatic hydrocarbon and decrease feed ethane selectivity to catalyst coke. Since the second stage produces a raffinate containing less aromatic hydrocarbon than does the first product, the third stage can be operated at a greater temperature with increased ethane conversion, increased selectivity to aromatic hydrocarbon, and decreased selectivity to catalyst coke.

Definitions

For the purpose of this specification and appended claims, the following terms are defined.

The term "$C_n$" hydrocarbon means hydrocarbon having n carbon atom(s) per molecule, wherein n is a positive integer. The term "$C_{n+}$" hydrocarbon means hydrocarbon having at least n carbon atom(s) per molecule. The term "$C_{n-}$" hydrocarbon means hydrocarbon having no more than n carbon atom(s) per molecule. The term "hydrocarbon" means a class of compounds containing hydrogen bound to carbon, and encompasses (i) saturated hydrocarbon, (ii) unsaturated hydrocarbon, and (iii) mixtures of hydrocarbon, including mixtures of hydrocarbon compounds (saturated and/or unsaturated) having different values of n.

The terms "alkane" and "paraffinic hydrocarbon" mean substantially-saturated compounds containing hydrogen and carbon only, e.g., those containing ≤1% (molar basis) of unsaturated carbon atoms. As an example, the term alkane encompasses $C_2$ to $C_{20}$ linear, iso, and cyclo-alkanes.

The term "unsaturate" and "unsaturated hydrocarbon" refer to one or more $C_{2+}$ hydrocarbon compounds which contain at least one carbon atom directly bound to another carbon atom by a double or triple bond. The term "olefin" refers to one or more unsaturated hydrocarbon compound containing at least one carbon atom directly bound to another carbon atom by a double bond. In other words, an olefin is a compound which contains at least one pair of carbon atoms, where the first and second carbon atoms of the pair are directly linked by a double bond. The term "aromatics" and "aromatic hydrocarbon" mean hydrocarbon compounds containing at least one aromatic core.

The term "Periodic Table" means the Periodic Chart of the Elements, as it appears on the inside cover of The Merck Index, Twelfth Edition, Merck & Co., Inc., 1996.

The term "reaction zone" or "reactor zone" mean a location within a reactor, e.g., a specific volume within a reactor, for carrying out a specified reaction. A reactor or reaction stage can encompass one or more reaction zones. More than one reaction can be carried out in a reactor, reactor stage, or reaction zone. For example, a reaction stage can include a first zone for carrying out first and second reactions and a second zone for carrying out a third reaction, where the first reaction (e.g., dehydrocyclization) can be the same as or different from the second reaction, and the third reaction (e.g., selective oxidation) can be the same as or different from the second reaction.

The term "selectivity" refers to the production (on a weight basis) of a specified compound in a catalytic reaction. As an example, the phrase "a light hydrocarbon conversion reaction has a 100% selectivity for aromatic hydrocarbon" means that 100% of the light hydrocarbon (weight basis) that is converted in the reaction is converted to aromatic hydrocarbon. When used in connection with a specified reactant, the term "conversion" means the amount of the reactant (weight basis) consumed in the reaction. For example, when the specified reactant is $C_4$ paraffinic hydrocarbon, 100% conversion means 100% of the $C_4$ paraffinic hydrocarbon is consumed in the reaction. Yield (weight basis) is conversion times selectivity.

The invention includes reacting a feed comprising non-aromatic hydrocarbon in a first stage to selectively convert at least a portion of the non-aromatic hydrocarbon to aromatic hydrocarbon. Representative feeds to the first stage will now be described in more detail. The invention is not limited to these feeds, and this description is not meant to foreclose other feeds within the broader scope of the invention.

Feeds

The feed typically comprises one or more non-aromatic hydrocarbon compounds, e.g., one or more light hydrocarbon (i.e., $C_2$ to $C_5$) compounds, such as paraffinic light hydrocarbon. For example, the feed can comprise ≥1 wt. % of light hydrocarbon based on the weight of the feed, such as ≥10 wt. %, or ≥25 wt. %, or ≥50 wt. %, or ≥75 wt. %, or ≥90 wt. %, or ≥95 wt. %. Optionally, the feed further comprises diluent. Diluent present in the feed's source (e.g., methane and/or $CO_2$ present in natural gas) and diluent added to the feed are within the scope of the invention. Diluent, when present, is typically included in the feed in an amount ≤60 wt. % based on the weight of the feed, e.g., ≤50 wt. %, such as ≤40 wt. %, or ≤30 wt. %, or ≤20 wt. %, or ≤10 wt. %. A feed constituent is diluent when it is substantially non-reactive under the specified reaction conditions in the presence of the specified catalyst, e.g., methane, molecular nitrogen, and inert atomic gasses such as argon.

The feed can contain $C_3$ and/or $C_4$ hydrocarbon e.g., (i) ≥20 wt. % propane, such as ≥40 wt. %, or ≥60 wt. and/or (ii) ≥20 wt. % butanes, such as ≥40 wt. %, or ≥60 wt. %. Although the feed can contain $C_{5+}$ hydrocarbon, the amount of $C_{5+}$ hydrocarbon when present is typically small, e.g., ≤20 wt. %, such as ≤10 wt. %, or ≤01 wt. %. Typically, the feed contains ≤10 wt. % of $C_{6+}$ saturated hydrocarbon, e.g., ≤5 wt. %.

The feed can contain methane, e.g., ≥1 wt. % methane, such as ≥10 wt. %, or ≥20 wt. %, or ≥60 wt. %. Even though methane is a diluent, i.e., it does not typically react to produce aromatic hydrocarbon or catalyst coke in the presence of the specified dehydrocyclization catalyst under the specified reaction conditions, its presence is beneficial. It is believed that this benefit results at least in part from a decrease in the partial pressure of the feed's $C_2$-$C_9$ hydrocarbon that is achieved when the feed further comprises methane. Decreasing the partial pressure of the feed's $C_2$-$C_9$ hydrocarbon, particularly the partial pressure of the feed's $C_2$-$C_5$ hydrocarbon, has been found to lessen the amount of catalyst coke formed under the reaction conditions specified for feed conversion to aromatic hydrocarbon. Typically, the feed comprises a total of ≤10 wt. % of impurities such as CO, $CO_2$, $H_2S$, and total mercaptan; e.g., ≤1 wt. %, or ≤0.1 wt. %. Optionally, the feed comprises molecular hydrogen, e.g., ≥1 wt. % molecular hydrogen based on the weight of the feed, such as ≥5 wt. %.

In certain aspects, the feed comprises ethane in an amount $A_1$, where $A_1$ is ≥1 wt. %, based on the weight of the feed. In these aspects, $A_1$ is typically ≥5 wt. %, e.g., ≥10 wt. %, such as in the range of from 10 wt. % to 40 wt. %. Suitable feeds include those containing a major amount of ethane, e.g., $A_1$>50 wt. % based on the weight of the feed, such as ≥75 wt. %, or ≥90 wt. %, or ≥95 wt. %. One representative feed comprises (i) ≥10 wt. % ethane, such as in the range of from 10 wt. % to 40 wt. %; and further comprises (ii) 1 wt. % to 40 wt. % methane, (iii) 20 wt. % to 50 wt. % propane, and (iv) 20 wt. % to 50 wt. % butanes. In other aspects, $A_1$ is <1 wt. %, e.g., ≤0.1 wt. %, or ≤0.1 wt. %.

Optionally, the feed contains unsaturated $C_2$+ hydrocarbon, such as $C_2$-$C_5$ unsaturated hydrocarbon. When present, the amount of $C_{2+}$ unsaturated hydrocarbon (e.g., $C_2$-$C_5$ unsaturated hydrocarbon) is typically ≤20 wt. %, e.g., ≤10 wt. %, such as ≤1 wt. %, or ≤0.1 wt. %, or in the range of from 0.1 wt. % to 10 wt. %. More particularly, the feed is generally one that is substantially-free of aromatic hydrocarbon, where substantially-free in this context means an aromatic hydrocarbon content that is <1 wt. % based on the weight of the feed, such as ≤0.1 wt. %, or ≤0.01 wt. %, or ≤0.001 wt. %. One representative feed comprises <1 wt. % ethane; ≤1 wt. % of aromatic hydrocarbon; and ≥1 wt. % of $C_{3+}$ paraffinic hydrocarbon, e.g., ≥10 wt. % of a mixture of $C_3$ and $C_4$, such as ≥50 wt. %, or ≥75 wt. %, or in the range of 80 wt. % to 99 wt. %. Another representative feed comprises (i) 10 wt. % to 40 wt. % ethane and ≤1 wt. % of aromatic hydrocarbon; with the feed further comprising (ii) 1 wt. % to 40 wt. % methane, (iii) 20 wt. % to 50 wt. % propane, and (iv) 20 wt. % to 50 wt. % butanes.

The feed's light hydrocarbon can be obtained from one or more sources of hydrocarbon, e.g., from natural hydrocarbon sources such as those associated with producing petroleum, or from one or more synthetic hydrocarbon sources such as catalytic and non-catalytic reactions. Examples of such reactions include, catalytic cracking, catalytic reforming, coking, steam cracking, etc. Synthetic hydrocarbon sources include those in which hydrocarbon within a geological formation has been purposefully subjected to one or more chemical transformations. The feed can include recycle components, e.g., portions of the first and/or second product, such as portions of the first and/or second raffinate. Such recycle, when used, can include, e.g., methane, molecular hydrogen, and $C_{2+}$ hydrocarbon, typically $C_2$ to $C_5$ hydrocarbon.

In certain aspects, the source of light hydrocarbon includes natural gas, e.g., raw natural gas ("raw gas"). Natural gas is (i) a mixture comprising hydrocarbon, (ii) primarily in the vapor phase at a temperature of 15° C. and a pressure of 1.013 bar (absolute), and (iii) withdrawn from a geologic formation. Natural gas can be obtained, e.g., from one or more of petroleum deposits, coal deposits, and shale deposits. The natural gas can be one that is obtained by conventional productions methods but the invention is not limited thereto. Raw natural gas is a natural gas obtained from a geologic formation without intervening processing, except for (i) treatments to remove impurities such as water and/or any other liquids, mercaptans, hydrogen sulfide, carbon dioxide; and (ii) vapor-liquid separation, e.g., for adjusting the relative amounts of hydrocarbon compounds (particularly the relative amounts of $C_{4+}$ hydrocarbon compounds) in the natural gas; but not including (iii) fractionation with reflux. Conventional methods can be used for removing impurities and/or adjusting the relative amount of hydrocarbon compounds present in the feed, but the invention is not limited thereto. For example, certain components in the natural gas can be liquefied by exposing the natural gas to a temperature in the range of −57° C. to 15° C., e.g., −46° C. to 5° C., such as −35° C. to −5° C. At least a portion of the liquid phase can be separated in one or more vapor-liquid separators, e.g., one or more flash drums. One suitable raw natural gas comprises 3 mole % to 70 mole % methane, 10 mole % to 50 mole % ethane, 10 mole % to 40 mole % propane, and 5 mole % to 40 mole % butanes and 1 mole % to 10 mole % of total $C_5$ to $C_9$ hydrocarbon. In certain aspects, ≥50 wt. % of the feed comprises natural gas, such as raw natural gas, e.g., ≥75 wt. %, or ≥90 wt. %, or ≥95 wt. %.

Any form of raw gas can be used as a source material, although the raw gas is typically one or more of (i) gas obtained from a natural gas well ("Gas Well", Non-associated", or "Dry" gas), (ii) natural gas obtained from a condensate well ("Condensate Well Gas"), and (iii) casing head gas ("Wet" or "Associated" gas). Table 1 includes typical raw gas compositional ranges (mole %) and, parenthetically, typical average composition (mole %) of certain raw gasses.

TABLE 1

| Component | Associated Gas | Dry Gas | Condensate Well Gas |
|---|---|---|---|
| $CO_2$ | 0-50 (0.63) | 0-25 (0) | 0-25 (0) |
| $N_2$ | 0-50 (3.73) | 0-25 (1.25) | 0-25 (0.53) |
| $H_2S$ | 0-5 (0.57) | 0-5 (0) | 0-5 (0) |
| $CH_4$ | 0-80 (64.48) | 0-97 (91.01) | 0-98 (94.87) |
| $C_2H_6$ | 5-20 (11.98) | 2-10 (4.88) | 1-5 (2.89) |
| $C_3H_8$ | 2-10 (8.75) | 0.5-5 (1.69) | 0.1-5 (0.92) |
| i-butane | 0.1-5 (0.93) | 0.05-1 (0.14) | 0.1-5 (0.31) |
| n-butane | 1-5 (2.91) | 0.05-2 (0.52) | 0.05-2 (0.22) |
| i-pentane | 0.05-2 (0.54) | 0.01-1 (0.09) | 0.01-1 (0.09) |

In certain aspects, the feed comprises ≥75 wt. % Associated Gas, based on the weight of the feed, e.g., ≥90 wt. %, or ≥95 wt. %. Associated Gas is typically found with petroleum deposits, e.g., dissolved in the oil or as a free "gas cap" above the oil in a reservoir. In conventional petroleum production, the lack of effective natural transportation facilities, e.g., the lack of natural gas liquefaction and/or pipeline facilities, typically results in Associated Gas being stranded at or near the reservoir. This in turn can lead to undesirable natural gas flaring. Moreover, even in locations where pipeline facilities are available, Associated Gas may be excluded from the pipeline because it typically exceeds one or more of the following typical pipeline specifications: ≤12 wt. % ethane, ≤5 wt. % propane, ≤2 wt. % butanes, a Wobbe Index of from 49.01 MJ/sm$^3$ to 52.22 MJ/sm$^3$, and a heating value of from 36.07 MJ/sm$^3$ to 41.40 MJ/sm$^3$.

Since methane is not detrimental to the process, and is in at least some aspects beneficial, the invention obviates the need for costly and inefficient cryogenic methane separation facilities, such as one or more conventional cold boxes. Typically, obtaining the feed from the source material (e.g., natural gas, such as raw gas) does not include (i) exposing the feed, source material, or any intermediate thereof to a temperature ≤−37° C., e.g., ≤−46° C., such as ≤−60° C. Certain aspects of the invention do not include cryogenic processing, e.g., cryogenic methane separation is not used.

The invention therefore particularly advantageous in remote or under-developed locations, where (i) the lack of cryogenic methane separation facilities limits the utility of conventional natural gas aromatization processes, (ii) the lack of a pipeline or natural gas production infrastructure, may result in significant quantities of light hydrocarbon being flared or burned as fuel, and (iii) Associated Gas remains stranded at a remote location for lack of pipeline facilities or a failure to meet one or more specifications of an available pipeline. Small scale plants using the present process would allow effective recovery of these light hydrocarbon resources as liquid hydrocarbons.

The feed is conducted to a first stage, where it is reacted in the presence of at least one first stage catalyst in at least one reaction zone operating under catalytic dehydrocyclization conditions. The reaction converts at least a portion of the feed's light hydrocarbon to aromatic hydrocarbon and molecular hydrogen. Certain aspects of the first stage will now be described in more detail. The invention is not limited to these aspects, and this description is not meant to foreclose other aspects of the first stage within the broader scope of the invention.

First Stage

Referring to FIG. 1, at least one of the specified feeds 100 is conducted to reaction zone 110, the reaction zone being typically located within a reactor vessel (not shown). The reaction zone includes at least one catalyst having dehydrocyclization functionality for converting at least a portion of the feed's light hydrocarbon to aromatic hydrocarbon and molecular hydrogen. The catalyst comprises ≥10 wt. % of a molecular sieve component and ≥0.005 wt. % of a dehydrogenation component. When the molecular sieve component and dehydrogenation component together comprise less than 100 wt. % of the catalyst, ≥90 wt. % of the remainder of the catalyst can comprise a matrix component, such as ≥99 wt. % of the remainder. Certain aspects of the molecular sieve component, dehydrogenation component, and optional matrix component will now be described in more detail. The invention is not limited to these aspects, and this description is not meant to foreclose other molecular sieve components and/or other dehydrogenation components within the broader scope of the invention.

The catalyst typically comprises the molecular sieve component in an amount ≥20 wt. %, based on the weight of the catalyst, e.g., ≥25 wt. %, such as in the range of from 30 wt. % to 99.9 wt. %. In certain aspects, the molecular sieve component comprises aluminosilicate, e.g., ≥90 wt. % of at least one aluminosilicate. The aluminosilicate can be an un-substituted aluminosilicate, a substituted aluminosilicate, or a combination thereof. For example, the aluminosilicate can be in a form where at least a portion of its original metal has been replaced, e.g., by ion exchange, with other suitable metal (typically metal cation) of Groups 1-13 of the Periodic Table. Typically, the aluminosilicate includes zeolite aluminosilicate, e.g., ≥90 wt. % of at least one zeolite based on the weight of the aluminosilicate. The term zeolite includes those in which at least part of the aluminum is replaced by a different trivalent metal, such as gallium or indium.

The molecular sieve component typically comprises ≥90 wt. % of one or more of the specified molecular sieves, e.g., ≥95 wt. %. In certain aspects, the molecular sieve component comprises at least one zeolite molecular sieve, e.g., ≥90 wt. % zeolite, such as ≥95 wt. %, based on the weight of the molecular sieve component. Although, the molecular sieve component can consist essentially of or even consist of zeolite, in alternative aspects the zeolite(s) is present in the molecular sieve component in combination with other (e.g., non-zeolitic) molecular sieve. The zeolite can be one that is in hydrogen form. e.g., one that has been synthesized in the alkali metal form, but is then converted from the alkali to the hydrogen form. Typically the zeolite is one having a medium pore size and a Constraint Index of 2-12 (as defined in U.S. Pat. No. 4,016,218). Examples of suitable zeolites include ZSM-5, ZSM-11, ZSM-12, ZSM-22, ZSM-23, ZSM-35, ZSM-48, including and mixtures and intermediates thereof such as ZSM-5/ZSM-11 admixture. ZSM-5 is described in U.S. Pat. Nos. 3,702,886 and Re. 29,948. ZSM-11 is described in U.S. Pat. No. 3,709,979. A ZSM-5/ZSM-11 intermediate structure is described in U.S. Pat. No. 4,229,424. ZSM-12 is described in U.S. Pat. No. 3,832,449. ZSM-22 is described in U.S. Pat. No. 4,556,477. ZSM-23 is described in U.S. Pat. No. 4,076,842. ZSM-35 is described in U.S. Pat. No. 4,016,245. ZSM-48 is described in U.S. Pat. No. 4,234,231. Optionally, the zeolite is one comprising at least one set of pores of substantially uniform size extending through the molecular sieve, wherein geometric mean of the cross-sectional dimensions of each of the sets of pores is >5 Å, or >5.3 Å, e.g., ≥5.4 Å such as ≥5.5 Å, or in the range of 5 Å to 7 Å, or 5.4 Å to 7 Å. ZSM-5 and/or ZSM-12 are suitable, particularly H-ZSM-5. For example, the molecular sieve component can comprise ≥90 wt. % of (A) ZSM-5 and/or (B) ZSM-12, based on the weight of the molecular sieve component, e.g., ≥95 wt. % of H-ZSM-5. In certain aspects, the molecular sieve has a relatively small crystal size, e.g., small crystal ZSM-5, meaning ZSM-5 having a crystal size ≤0.05 µm, such as in the range of 0.02 µm to 0.05 µm. Small crystal ZSM-5 and the method for determining molecular sieve crystal size are disclosed in U.S. Pat. No. 6,670,517, which is incorporated by reference herein in its entirety.

In other aspects, the molecular sieve component comprises at least one molecular sieve of the MCM-22 family, e.g., MCM-22 alone or in combination with other molecular sieve such as one or more of the specified zeolites. As used herein, the term "molecular sieve of the MCM-22 family" (or "material of the MCM-22 family" or "MCM-22 family material" or "MCM-22 family zeolite") includes one or more of:

(i) molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

(ii) molecular sieves made from a common second degree building block, being a 2-dimensional tiling of such MWW framework topology unit cells, forming a monolayer of one unit cell thickness, preferably one c-unit cell thickness;

(iii) molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and (iv) molecular sieves made by any regular or random 2-dimensional or 3-dimensional combination of unit cells having the MWW framework topology.

The MCM-22 family includes those molecular sieves having an X-ray diffraction pattern including d-spacing maxima at 12.4±0.25, 6.9±0.15, 3.57±0.07 and 3.42±0.07 Angstrom. The X-ray diffraction data used to characterize the material are obtained by standard techniques using the K-alpha doublet of copper as incident radiation and a diffractometer equipped with a scintillation counter and associated computer as the collection system.

Materials of the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), and mixtures thereof. Related zeolite UZM-8 is also suitable for use as the molecular sieve component.

When the molecular sieve component comprises at least one aluminosilicate, e.g., at least one zeolite, the aluminosilicate's silica:alumina ratio (substantially the same as the aluminosilicate's $Si:Al_2$ atomic ratio) is typically ≥2, e.g., in the range of from 5 to 100. The silica:alumina ratio is meant to represent the $Si:Al_2$ atomic ratio in the rigid anionic framework of the crystalline aluminosilicate. In other words, aluminum in (i) any matrix or binder or (ii) in cationic or other form within the crystalline aluminosilicate's channels is excluded from the silica:alumina ratio. Alternatively or in addition, the catalyst can be made more resistant to deactivation (and increase aromatic hydrocarbon yield) by including phosphorous with the molecular sieve component. Conventional methods can be utilized for adding phosphorous, but the invention is not limited thereto. When used, the amount of phosphorous is typically ≥1 wt. % based on the weight of the molecular sieve component. For example, when the molecular sieve component comprises aluminosilicate, the phosphorous:aluminum atomic ratio can be in the range of from 0.01 to 1. Zeolite having a higher silica:alumina ratio can be utilized when a lower catalyst acidity is desired, e.g., in the range of from 44 to 100, such as from 50 to 80, or 55 to 75.

In addition to the molecular sieve component, the catalyst comprises ≥0.005 wt. %, based on the weight of the catalyst, of a dehydrogenation component, e.g., at least one dehydrogenation metal. The dehydrogenation component can comprise one or more neutral metals selected from Groups 3 to 13 of the Periodic Table of the Elements, such as one or more of Ga, In, Zn, Cu, Re, Mo, W, La, Fe, Ag, Pt, and Pd, and/or one or more oxides, sulfides and/or carbides of these metals. Typically, the dehydrogenation component comprises ≥90 wt. % of the one or more of the specified dehydrogenation metals and/or oxide thereof, e.g., ≥95 wt. %, or ≥99 wt. %. For example, the dehydrogenation component can comprise ≥90 wt. % of (A) Ga and/or (B) Zn, including oxides thereof. Typically, the catalyst comprises ≥0.01 wt. % of the dehydrogenation component, based on the weight of the catalyst. For example, the catalyst can comprise ≥0.1 wt. % of the dehydrogenation component, such as ≥0.5 wt. %, or ≥1 wt. %. Those skilled in the art will appreciate that when the dehydrogenation component comprises one or more metals of greater catalytic dehydrogenation activity, e.g., Pt, and/or Pd, a lesser amount of dehydrogenation component is needed, e.g., in the range of 0.005 wt. % to 0.1 wt. %, based on the weight of the catalyst, such as 0.01 wt. % to 0.6 wt. %, or 0.01 wt. % to 0.05 wt. %. When the dehydrogenation component comprises one or more metals of lesser dehydrogenation activity, e.g., one or more of Ga, In, Zn, Cu, Re, Mo, and W, a greater amount of dehydrogenation component is needed, e.g., in the range of 0.05 wt. % to 10 wt. %, based on the weight of the catalyst, such as 0.1 wt. % to 5 wt. %, or 0.5 wt. % to 2 wt. %.

The dehydrogenation component can be provided on the catalyst in any manner, for example by conventional methods such as impregnation or ion exchange of the molecular sieve with a solution of a compound of the relevant metal, followed by conversion of the metal compound to the desired form, namely neutral metal, oxide, sulfide and/or carbide. As specified in connection with the molecular sieve component, at least part of the dehydrogenation metal may also be present in the crystalline framework of the molecular sieve. For one representative catalyst, (i) the dehydrogenation component comprises ≥95 wt. % of (A) Ga and/or (B) Zn, and (ii) the first molecular sieve component comprises ≥95 wt. % of H-ZSM-5.

In certain aspects, the dehydrogenation component comprises ≥99 wt. % of one or more of Ga, Zn, and In, and the molecular sieve component comprises ≥99 wt. % of ZSM-5-type zeolite that has been impregnated with the dehydrogenation metal component and/or ion exchanged with the dehydrogenation metal component. For example, the catalyst can comprise Ga-impregnated and/or In-impregnated H-ZSM-5, Ga-exchanged and/or In-exchanged H-ZSM-5, H-gallosilicate of ZSM-5 type structure and H-galloaluminosilicate of ZSM-5 type structure. Optionally, the catalyst includes (i) tetrahedral aluminum and/or gallium, which is present in the zeolite framework or lattice, and/or (ii)

octahedral gallium or indium, which is not present in the zeolite framework but present in the zeolite channels in close vicinity to the zeolitic protonic acid sites. While not wishing to be bound by any theory or model, the tetrahedral or framework Al and/or Ga is believed to contribute to acid function of the catalyst and octahedral or non-framework Ga and/or In is believed to contribute to the dehydrogenation function of the catalyst. Although typically the zeolite is impregnated or ion-exchanged with the dehydrogenation metal, other forms of zeolite can be used, such as H-galloaluminosilicate of ZSM-5 type structure having framework (tetrahedral) Si/Al and Si/Ga atomic ratios of about 10:1 to 100:1 and 15:1 to 150:1, respectively, and non-framework (octahedral) Ga of about 0.5 wt. % to 0 wt. %.

Besides the molecular sieve component and dehydrogenation component, the catalyst can further comprise an optional matrix component, e.g., one or more inorganic binders. A matrix component can be used, e.g., to make the catalyst more resistant to the temperatures and other conditions employed in the conversion reaction. The amount of matrix component is not critical. When present, the amount of matrix component is typically in the range of 0.01 times the weight of the molecular sieve component to about 0.9 times the weight of the molecular sieve component, e.g., in the range of 0.02 to 0.8. The matrix component can include active materials, such as synthetic or naturally occurring zeolites. Alternatively, or in addition, the matrix component can include clays and/or oxides such as alumina, silica, silica-alumina, zirconia, titania, magnesia or mixtures of these and other oxides. The matrix component can include naturally occurring materials and/or materials in the form of gelatinous precipitates or gels including mixtures of silica and metal oxides. Clays may also be included with the oxide type binders to modify the mechanical properties of the catalyst or to assist in its manufacture. Alternatively or in addition, the matrix component can include one or more substantially inactive materials. Inactive materials suitably serve as diluents to control the amount of conversion so that products may be obtained economically and orderly without employing other means for controlling the rate of reaction. These materials may be incorporated into naturally occurring clays, e.g., bentonite and kaolin, to improve thermal and strength properties (e.g., crush strength) of the catalyst under catalytic conversion conditions. Alternatively or in addition to any phosphorous added to or impregnated into the molecular sieve component, the matrix component can optionally include phosphorous, e.g., to lessen catalyst acidity. Those skilled in the art will appreciate that lessening catalyst acidity decreases the amount of catalyst coke produced during the catalytic conversion of the feed's light hydrocarbon to aromatic hydrocarbon. Suitable phosphorous-containing matrices are disclosed in U.S. Pat. No. 5,026,937, which is incorporated by reference herein in its entirety. The matrix component is optional. In certain aspects, the catalyst is substantially-free of matrix, e.g., contains ≤1 wt. % of matrix, such as ≤0.1 wt. %. In particular, the catalyst can be substantially free of binder, e.g., contains ≤1 wt. % of binder, such as ≤0.1 wt. %. For example, the catalyst's molecular sieve component can comprises ≥95 wt. % of substantially binder-free molecular sieve, e.g., ≥95 wt. % of substantially binder-free ZSM-5, and in particular small crystal H-ZSM-5.

The catalyst can be one that has been subjected to one or more treatments, e.g., a selectivation treatment to increase selectivity for producing desired aromatic hydrocarbon compounds such as paraxylene. For example, the catalyst's molecular sieve component can comprise at least one selectivated molecular sieve. The selectivation can be carried out before introduction of the catalyst into the reactor and/or in-situ in the reactor, e.g., by contacting the catalyst with a selectivating agent, such as at least one organosilicon in a liquid carrier and subsequently calcining the catalyst at a temperature of 350 to 550° C. This selectivation procedure can be repeated two or more times and alters the diffusion characteristics of the catalyst such that the formation of para-xylene over other xylene isomers is favored. Such a selectivation process is described in detail in U.S. Pat. Nos. 5,633,417 and 5,675,047, which are incorporated by reference herein in their entirety.

Typically, the catalyst has a surface area as measured by nitrogen physisorption in the range of from 100 m$^2$/g to 600 m$^2$/g, e.g., in the range of from 200 m$^2$/g to 500 m$^2$/g. When the catalyst comprises aluminosilicate which includes phosphorous, the phosphorous:aluminum atomic ratio is typically in the range of from 0.01 to 0.5. For example, the catalyst can contain ≥10 wt. % of phosphorous-modified alumina, such as ≥15 wt. %, or in the range of from 10 wt. % to 20 wt. %.

Referring again to FIG. 1, the feed's light hydrocarbon is exposed to a catalytically effective amount of the specified catalyst under catalytic dehydrocyclization conditions in reaction zone 110 that are effective for converting at least a portion of the feed's light hydrocarbon to aromatic hydrocarbon and molecular hydrogen. In certain aspects, the catalytic dehydrocyclization conditions include exposing the feed to a temperature $T_1$ in the range of from 400° C. to 630° C., and a pressure $P_1$ that is sufficient for carrying out the dehydrocyclization. Typically, $T_1$ is in the range of from 450° C. to 605° C. Typically, $P_1$ is ≥20 psia (137.9 kPa) e.g., ≥35 psia (241.3 kPa), such as in the range of from 35 psia (241.3 kPa) to 300 psia (2070 kPa). For example, $P_1$ can be in the range of from 35 psia (241.3 kPa) to 300 psia (2070 kPa), such as 37 psia (255.1 kPa) to 80 psia (522 kPa), or 40 psia (275.8 kPa) to 80 psia (522 kPa), or 45 psia (310.2 kPa) to 80 psia (522 kPa). Generally, the catalytic dehydrocyclization conditions further include a weight hourly space velocity (WHSV) in the range of from 0.1 hr$^{-1}$ to 20 hr$^{-1}$, e.g., 0.2 hr$^{-1}$ to 5 hr$^{-1}$, such as 0.3 hr$^{-1}$ to 1.0 hr$^{-1}$. WHSV is based on the feed's $C_{2+}$ hydrocarbon content, and is the hourly rate of the feed's $C_{2+}$ hydrocarbon (in grams) per gram of catalyst. In a particular aspect, the average temperature across any reaction zone within stage 1 (and across any catalyst bed located within a reaction zone of stage 1) is ≤600° C. Typically, the feed is not exposed to a temperature ≥630° C. at the inlet to reaction zone 110.

Since the dehydrocyclization reaction of stage 1 is carried out at a relatively large pressure (relative to the pressure of stage 3), hydrogen is produced by the dehydrocyclization reaction at a relatively large partial pressure. It was expected that the large partial pressure of hydrogen would suppress feed dehydrogenation, leading to a decrease in the yield of $C_{6+}$ hydrocarbon such as aromatic hydrocarbon. Surprisingly this has been found to not be the case: the relatively large hydrogen partial pressure in stage 1 has been found to lessen the rate of catalyst coke accumulation with little or no decrease in the yield of aromatic hydrocarbon. For example, when the dehydrocyclization conditions of the first stage include a pressure $P_1$≥35 psia (241.3 kPa), the dehydrocyclization reaction can be sustained for a time duration ≥50 hours, e.g., ≥100 hours, such as ≥200 hours, or ≥500 hours with a decrease in the yield of $C_{6+}$ hydrocarbon of ≥10%, e.g., ≥5%, such as ≥1%.

Reaction zone 110 contains at least one bed of the specified catalyst. The catalyst can be in particulate form, with the dehydrocyclization reaction taking place as the feed traverses the catalyst bed. The catalyst bed can be one or more of a fixed, moving, or fluidized catalyst bed. In a fixed bed (also called a packed bed), the catalyst remains stationary in the reaction zone. The feed enters the reaction zone proximate to the upstream end of reactor 101. After the dehydrocyclization reaction is carried out in the bed, the first product exits the reaction zone near the downstream end of reactor 110. The reaction zone within the reactor establishes a fixed reference frame, and the catalyst bed is "fixed" in the sense that it is substantially immobile with respect to the fixed reference frame during the dehydrocyclization reaction, e.g., ≥90 wt. % of catalyst associate with a bed is located in substantially fixed positions within the bed. The reactor can be, e.g., an adiabatic single bed, a multi-tube surrounded with heat exchange fluid or an adiabatic multi-bed with internal heat exchange, among others. For example, reaction zones 110 and/or zone 120 can each comprise a plurality (e.g., three) of fixed catalyst, optionally with provisions for adding heat to the process (i) at one or more locations between at least two of the beds, and/or (ii) upstream and/or downstream of the reaction zone(s). At least one substantially similar second reaction zone (not shown) can be operated in parallel with reaction zone 110, so that reaction zone 110 can be operated in reaction mode while the second reaction zone is operated in regeneration mode, to regenerate the second reaction zone's catalyst. Continuous or semi-continuous operation can be carried out by alternating reaction and regeneration modes in the reactor 110 and the second reactor. The reaction zones of the first stage (e.g., zone 110 and/or zone 120) can be operated in dehydrocyclization mode for an average cycle time ≥50 hours, e.g., ≥75 hours, such as ≥100 hours, or ≥120 hours, at an aromatics yield in each zone that is ≥75% of that attained at the start of dehydrocyclization mode, e.g., ≥90%, such as ≥95%.

In a moving bed, particles of the specified catalyst flow under the influence of an external force such as gravity. The catalyst particles substantially maintain their relative positions to one another during the flow, resulting in a movement of the bed with respect to the fixed reference frame. Average flow of the specified feed with respect to the catalyst flow can be concurrent, countercurrent, or cross-current.

In a fluidized bed, a fluidizing medium (typically in the vapor phase) is conducted through the catalyst bed at a velocity sufficient to suspend the catalyst particles within the bed. The bed suspended catalyst particles typically has the appearance of a boiling fluid. The fluidizing medium's velocity is selected such that the fluidizing medium exerts a sufficient force on the catalyst particles to substantially balance the weight of the catalyst bed.

Conventional fixed, moving, and/or fluidized beds can be used in reaction zone 110 and option reaction zone 120, but the invention is not limited thereto. In the reactor beds of stages 1 and 3, the temperature drop across a reactor bed is typically in the range of from 20° C. to 200° C., e.g., in the range of from 50° C. to 150° C.

Since conversion of light hydrocarbon to aromatic hydrocarbon is endothermic, it can be desirable to transfer heat to one or more reaction zones of the first stage. One way to do this is illustrated schematically in FIG. 2, where the first stage includes two reaction zones. As shown, feed 100 is conducted to first reaction zone 110 which contains at least one bed of the specified catalyst. Reaction effluent comprising molecular hydrogen, aromatic hydrocarbon, an unconverted portion of the feed's light hydrocarbon, reaction by-products, etc., is conducted away from first reaction zone 110 via conduit 111 to a heat transfer stage 112. Heat is transferred to the reaction effluent in heat transfer 112, and the heated effluent is conducted via conduit 113 to second reaction zone 120. The method for carrying out the heat transfer of stage 112 is not critical, provided it is capable of transferring to the first reaction zone's effluent sufficient heat to replace at least a portion of the heat consumed in the endothermic dehydrocyclization reaction of the first reaction zone, so that the desired conversion and selectivity can be achieved in the second reaction zone. For example, stage 112 can include direct and/or indirect heat transfer. Direct heat transfer can be carried out using methods disclosed in U.S. Pat. No. 5,026,937, for example, which include selective combustion of molecular hydrogen in the first reaction zone's effluent. Indirect heat transfer can be carried out using one or more heat exchangers, for example. The heat transfer can include electric heating, which can utilize electric power. For example, electric power can be produced proximate to the process using one or more electric generators. Suitable electric power sources include those which (i) produce electricity by chemical and/or electrochemical conversion and/or (ii) produce electric power from one or more mechanical power sources, e.g., from shaft power. Shaft power can be produced by combusting one or more combustible materials in turbo machinery, for example. Suitable combustible materials, e.g., hydrocarbon, molecular hydrogen, carbon monoxide, etc., can be separated from one or more of the feed's source material, the feed, the first product, the second product, and the raffinate. Besides adding heat, selectively removing molecular hydrogen from the first stage effluent has been found to desirably increase selectivity to aromatic hydrocarbon in the second zone of the first stage and in the third stage.

Figure 2:
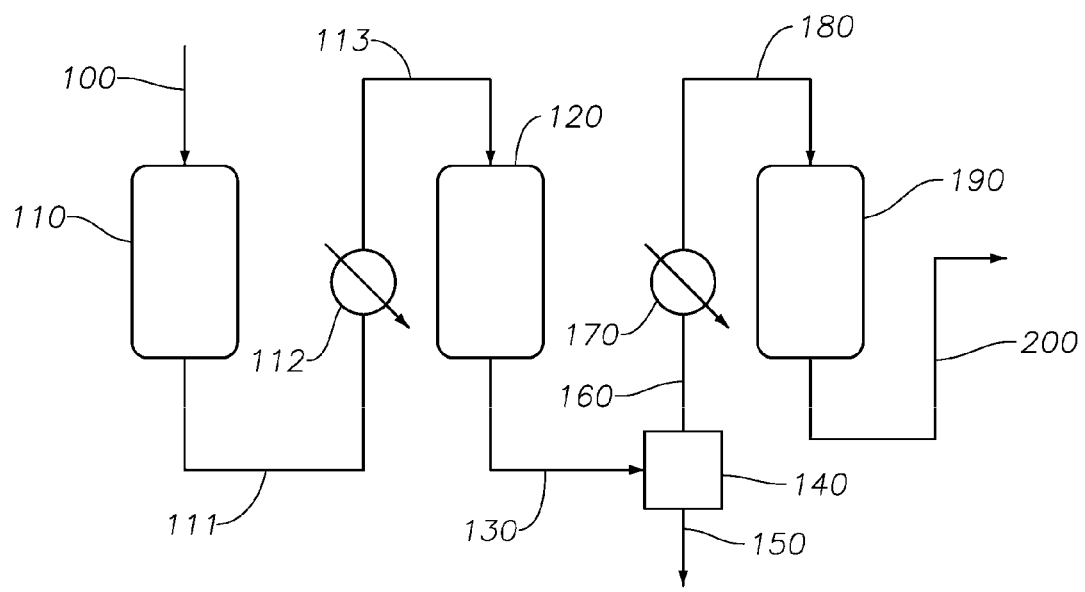
FIG. 2 schematically illustrates certain aspects of the invention in which the first stage includes two reaction zones.

The heated effluent is reacted in reaction zone 120 to produce the first product. The number of catalyst beds, the bed configuration, the dehydrocyclization catalyst, and dehydrocyclization conditions can be the same as or different from those of reaction zone 110, but are typically substantially the same. The first and second reaction zones can be located within the same reaction vessel, but this is not required. As shown in FIGS. 1 and 2, where like index numbers in each figure refer to features performing substantially the same function, the first product is conducted away from the first stage via line 130.

When the feed of line 100 comprises $A_1$ wt. % ethane, wherein $A_1 \geq 1$ and the first stage is operated under the specified conditions, the first product comprises (i) ≥1 wt. % aromatic hydrocarbon, (ii) molecular hydrogen, (iii) $A_2$ wt. % ethane, wherein $A_2 \geq 0.75 \cdot A_1$, such as $A_2 \geq A_1$, or $A_2 \geq 1.5 \cdot A_1$, or $A_2 \geq 2 \cdot A_1$. The amount of aromatic hydrocarbon in the first product can be, e.g., ≥5 wt. %, such as ≥10 wt. %, or in the range of from 1 wt. % to 90 wt. %, or 10 wt. % to 75 wt. %.

When the feed comprises ethane and $C_{3+}$ light hydrocarbon, the catalyst and conditions in reaction zone 110 (and optional reaction zone 120, when present) can be selected from among those specified for the first stage to provide (i) ≤25 wt. % conversion of the feed's ethane, such as ≤10 wt. %, or ≤5 wt. %, or ≤1 wt. % and (ii) ≥25 wt. % conversion of the feed's $C_{3+}$, e.g., ≥50 wt. %, or ≥75 wt. %. Typically, one or more of the catalyst mass, catalyst volume, and feed flow rate are selected to achieve a $C_{3+}$ conversion ≥90%, such as ≥95%, or ≥98%. In certain aspects, $A_1 \geq 10$, and the feed further comprises 1 wt. % to 40 wt. % methane; 20 wt. % to 50 wt. % propane; and 20 to 50 wt. % butanes. In these aspects, the first product can comprise ≥10 wt. % aromatic hydrocarbon, molecular hydrogen, $A_2$ wt. % ethane, 1 wt. % to 40 wt. % methane, ≤2 wt. % propane, and ≤1 wt. % butanes. Typically, in these aspects, $A_2 \geq A_1$, e.g., $A_2 \geq 1.5 \cdot A_1$, such as $A_2 \geq 2 \cdot A_1$. The increased ethane content of the first product compared to the feed is believed to result from hydrogenolysis of $C_{3+}$ feed components. Although the first stage dehydrocyclization reaction is selective for aromatic hydrocarbon and molecular hydrogen, the reaction typically produces (i) ethane conversion products such as methane and catalyst coke and (ii) $C_{3+}$ conversion products such as ethane, methane, and catalyst coke. Accordingly, the amount of ethane in the first product can be considerably larger than that in the feed. For example, in aspects when the feed comprises <1 wt. % ethane, such as ≤0.1 wt. % ethane, ≤1 wt. % of aromatic hydrocarbon, and ≥1 wt. % of $C_{3+}$ paraffinic hydrocarbon, then the first product can comprise ≥10 wt. % aromatic hydrocarbon, molecular hydrogen, $A_2$ wt. % ethane, 1 wt. % to 40 wt. % methane, ≤2 wt. % propane, and ≤1 wt. % butanes, wherein $A_2 \geq 1$ wt. %, e.g., ≥5 wt. %, such as ≥10 wt. %.

Those skilled in the art will appreciate that within the ranges of process parameters specified for the first stage dehydrocyclization, there are process conditions which result in a maximum propane conversion to aromatic hydrocarbon "$X_{MP}$". Unlike conventional multi-stage processes, the first stage is typically operated at a propane conversion to aromatic hydrocarbon that is less than $X_{MP}$. Instead, when the feed to the first stage comprises propane and/or when propane is produced in the first stage, process conditions are generally selected so that the initial (start of run) propane conversion to aromatic hydrocarbon in stage one "$X_{1P}$" is ≤0.95·$X_{MP}$. Typically, $X_{1P} \leq 0.90 \cdot X_{MP}$, e.g., ≤0.85·$X_{MP}$, or ≤0.80·$X_{MP}$, or ≤0.75·$X_{MP}$. It has been found that operating stage one under conditions which provide $X_{1P} \geq X_{MP}$ leads to excessive catalyst coking, typically resulting in a shortened cycle time in fixed bed operation. The same effect is observed for conversion of butanes to aromatic hydrocarbon, but with less sensitivity to changes in stage 1 process conditions. Instead of operating at maximum conversion of butanes to aromatic hydrocarbon $X_{MB}$, the specified process conditions typically result in an initial (start of run) conversion of butenes to aromatic hydrocarbon ("$X_{1B}$") that is less than $X_{MB}$, e.g., $X_{1B} \leq 0.995 \cdot X_{MB}$, such as ≤0.99·$X_{MB}$, or ≤0.985·$X_{MB}$.

Second Stage

Returning to FIGS. 1 and 2, the first product is conducted away from the first stage via line 130 to a second stage 140 for extracting at least a portion of the first product's aromatic hydrocarbon. Any convenient method can be utilized for extracting aromatic hydrocarbon from the first product, including, e.g., one or more of exposing the first mixture to a membrane selective for admitting (or excluding) aromatic hydrocarbon, separation by condensation of compounds having a higher boiling point (e.g., fractionation), chemical extraction, etc. Conventional methods can be utilized to do so, but the invention is not limited thereto.

In certain aspects, heat is transferred away from the first product of line 130 in order to condense at least a portion of the first product's aromatic hydrocarbon into the liquid phase. Any convenient method can be utilized for carrying out the heat transfer, e.g., using one or more heat exchangers (not shown). One or more separator drums (also called knock-out drums) located in stage 140 are employed for separating the liquid phase portion, which is then extracted via line 150. The vapor-phase material removed from the separator drum (a raffinate) typically comprises ≥90 wt. % of the remainder of the first product after extraction of the aromatic hydrocarbon portion, e.g., ≥99 wt. %. The raffinate is conducted away from stage 140 via conduit 160.

Certain aspects, such as those shown in FIGS. 1 and 2, include a second heat transfer 170. For example, when the first product has been subjected to cooling in connection with the aromatic hydrocarbon extraction, stage 170 can be utilized for heating the raffinate to a temperature sufficient for carrying out the dehydrocyclization reaction in the third stage. Any convenient heating method can be used, such as those described in connection with stage 112.

Typically, the extract comprises ≥50 wt. % of the first product's aromatic hydrocarbon, e.g., ≥75 wt. %, such as ≥90 wt. %, or ≥95 wt. %. The raffinate generally comprises ethane and molecular hydrogen, and typically further comprises methane. For example, the raffinate can comprise $A_3$ wt. % of ethane, where $A_3 > A_2$, e.g., $A_3 > 1.25 \cdot A_2$, such as $A_3 > 2 \cdot A_2$, or $A_3 > 5 \cdot A_2$. Generally $A_3$ is ≥1 wt. %, even when the feed contains <1 wt. % ethane ($A_1 < 1$), e.g., $A_3$ can be ≥5 wt. %, such as ≥10 wt. %. In other words, the raffinate typically has a greater ethane content than does the first product. In a particular aspect, the raffinate comprises (A) ≥75 wt. % of the first product's ethane, e.g., ≥90 wt. %, such as ≥95 wt. %; and (B) ≤10 wt. % of the first product's aromatic hydrocarbon, e.g., ≤5 wt. %, such as ≤1 wt. %. Typically, the raffinate further comprises (a) ≥10 wt. % of the first product's molecular hydrogen, e.g., ≥25 wt. %, such as ≥50 wt. %, or ≥95 wt. %, and/or ≥10 wt. % of the first product's methane, e.g., ≥25 wt. %, such as ≥50 wt. %, or ≥95 wt. %.

Although substantially all gaseous, non-aromatic compounds in the first product are typically transferred to the raffinate, this is not required. For example, the second stage can include separating and conducting away a first portion of the first product's molecular hydrogen, with a second portion transferred to the raffinate. Doing so can provide sufficient molecular hydrogen to the third stage for lessening catalyst coke accumulation, but not so much as to undesirably decrease the amount of dehydrocyclization. Typically the first portion comprises 20 wt. % to 80 wt. % of the first product's molecular hydrogen, with the second portion comprising ≥95 wt. % of the remainder of the first product's molecular hydrogen. Alternatively or in addition, a first portion of the first product's methane can be separated and conducted away from the second stage, with a second portion transferred to the raffinate. This can be desirable when the first raffinate would otherwise contain more methane than is needed for lessening the ethane partial pressure in stage 3 into a desirable range.

Third Stage

Referring again to FIGS. 1 and 2, the third stage includes conducting the heated raffinate away from stage 170 via conduit 180 to reaction zone 190 for carrying out additional catalytic dehydrocyclization in the presence of a second dehydrocyclization catalyst. A second product 200 comprising additional aromatic hydrocarbon and additional molecular hydrogen is conducted away from reaction zone 190. If desired, at least a portion of the second product's aromatic hydrocarbon can be separated and conducted away, i.e., for storage and/or further processing. For example, the separated aromatic hydrocarbon can be combined with extract 150 (or an aromatic hydrocarbon component thereof) to produce an aromatic mixture. Extract 150, second product 200, and the aromatic mixture can be used, e.g., as blend components for transportation fuels, as feed for petrochemical processes, e.g., alkylation and/or polymerization for producing one or more of styrene, phenol, nylon, polyurethanes, and xylenes such as paraxylene.

Reaction stage 190 includes a bed of the second dehydrocyclization catalyst. The second catalyst can be selected from among the same catalysts specified for use in stage 1 (the first catalyst), although typically the second catalyst has a greater acidity than does the first catalyst. For example, the molecular sieve component comprises ≥90 wt. % of an aluminosilicate in hydrogen form, the aluminosilicate having a constraint index in the range of from 2-12 (e.g., small crystal, H-ZSM-5). Typically, (i) the second catalyst has a silica:alumina ratio in the range of from 3 to 60, e.g., from 10 to 40, such as from 15 to 35, and (ii) the catalyst comprises <0.01 wt. % phosphorus. The form of catalyst bed can be selected from among the same bed forms utilized in reaction zone 110 or 120, e.g., one or more fixed bed, moving bed, or fluidized bed. In a particular aspect, the average temperature across any reaction zone within stage 1 (and across any catalyst bed located within a reaction zone of stage 1) is ≤700° C. Typically, the feed is not exposed to a temperature ≥700° C. at the inlet to reaction zone 110.

Third stage reaction conditions (e.g., in zone 190) generally include catalytic dehydrocyclization conditions such as a temperature $T_2$ in the range of from 450° C. to 700° C., and a pressure $P_2 \leq 35$ psia (241.3 kPa). Typically, $T_1 \leq 0.90 \cdot T_2$, e.g., $T_1 \leq 0.85 \cdot T_2$, such as $T_1 \leq 0.80 \cdot T_2$. The pressure in stage 3 is less than the pressure in stage 1, e.g., $P_2 \leq 0.95 \cdot P_1$, such as $P_2 \leq 0.90 \cdot P_1$, or $P_2 \leq 0.85 \cdot P_1$, or $P_2 \leq 0.80 \cdot P_1$. Typically, reaction conditions include $T_2$ in the range of from 500° C. to 675° C. and $P_2 \leq 34$ psia (234.4 kPa), e.g., ≤32 psia (220.6 kPa), such as ≤30 psia (207 kPa), or in the range of from 10 psia (68.9 kPa) to 35 psia (241.3 kPa) or from 12 psia (82.8 kPa) to 34 psia (234.4 kPa). Generally, the reaction is carried out at a $C_{2+}$ hydrocarbon WHSV of the specified raffinate with respect to the second catalyst in the range of from 0.1 $hr^{-1}$ to 20 $hr^{-1}$, e.g. 0.2 $hr^{-1}$ to 5 $hr^{-1}$, or 0.3 $hr^{-1}$ to 1 $hr^{-1}$. In congruence with the first stage's WHSV, the WHSV of the third stage is based on the raffinate's $C_{2+}$ hydrocarbon content, and is the hourly rate of the raffinate's $C_{2+}$ hydrocarbon (in grams) per gram of catalyst. Since hydrocarbon is separated from the first product in the second stage, the mass flow rate of $C_{2+}$ hydrocarbon to reaction zone 190 is typically less than the mass flow rate of feed to the first reaction zone 110. Those skilled in the art will appreciate that $T_1$ and $T_2$ represent average temperatures across a reaction zone, or more particularly, across a catalyst bed located within a reaction zone. Average temperature is calculated by adding the zone's inlet temperature to the zone's outlet temperature, and then dividing the sum by 2. $P_1$ and $P_2$ are not average pressures. Instead, they correspond to the inlet pressure at the specified reaction zone, e.g., reaction zone 110 for $P_1$ and reaction zone 190 for $P_2$.

Unlike stage 1, it has been found that increased reaction pressure in stage 3 (i) decreases the yield of aromatic hydrocarbon and (ii) increases the rate of catalyst coke accumulation. A stage 3 pressure of $P_2 \leq 35$ psia (241.3 kPa) is generally needed to achieve a stage 3 cycle time ≥50 hours.

Those skilled in the art will appreciate that within the ranges of process parameters specified for the third stage dehydrocyclization, there are process conditions which result in a maximum ethane conversion to aromatic hydrocarbon "$X_{ME}$". Unlike conventional multi-stage processes, the third stage typically is not operated at $X_{ME}$. Instead, process conditions are generally selected so that the initial (start of run) conversion of ethane to aromatic hydrocarbon in stage three "$X_3$" is less than $X_{ME}$, e.g., $\leq 0.90 \cdot X_{ME}$. Typically, $X_3 \leq 0.85 \cdot X_{ME}$, e.g., $\leq 0.80 \cdot X_{ME}$, or $\leq 0.75 \cdot X_{ME}$. It has been found that operating stage three under conditions which provide $X_3 \geq X_{ME}$ lead to excessive catalyst coking, which typically necessitates a shortened cycle time in fixed bed operation.

Contrary to expectations, it has been found that it is detrimental to operate reaction zone 190 at a temperature sufficient for maximum conversion of the raffinate's ethane, typically $T_2 \geq 700°$ C. Doing so is observed to result in a decrease in selectivity to the desired aromatic hydrocarbon product. It also has been found that operating reaction zone 190 at a temperature >700° C. in the presence of the specified raffinate can lead to a chemical conversion of the catalyst's dehydrogenation component and a loss of catalytic dehydrocyclization activity, particularly when the dehydrogenation component comprises one or more oxide of Zn. While not wishing to be bound by any theory or model, it is believed that utilizing a temperature >700° C. results in a conversion from the oxide form to a metallic form of Zn, which has a greater vapor pressure than does the oxide form. The loss of catalytic dehydrocyclization activity is thus attributed at least partially to the evaporation of Zn from the catalyst. Typically, total ethane conversion in the third stage is ≤60%, e.g., ≤50, such as ≤40%, or in the range of from 25% to 60%, or 30% to 55%, or 30% to 50%, or 30% to 40%.

As is the case for the first stage, the third stage can include one or more additional reaction zones, e.g., a second reaction zone (not shown). The second zone of the third stage can be one that is substantially the same as reaction zone 190, namely of substantially the same bed configuration and contain substantially the same amount of substantially the same catalyst as is used in reaction zone 190. Reaction zone 190 can be operated in reaction mode while the second reaction zone is operated in regeneration mode, to regenerate the second reaction zone's catalyst. As in the first stage, continuous or semi-continuous operation can be carried out by alternating reaction and regeneration modes in the reactor 190 and the second reaction zone. Zone 190 can be operated in dehydrocyclization mode for an average cycle time ≥50 hours, e.g., ≥75 hours, such as ≥100 hours, or ≥120 hours, at an aromatics yield that is ≥95% of that attained at the start of dehydrocyclization mode, e.g., ≥90%, such as ≥75%.

Catalysts of zones 110, 120, and 190 are typically regenerated at a temperature ≤700° C. Exceeding this temperature during regeneration has been found to result in catalyst de-alumination and/or loss of structure, leading to an undesirable loss of catalyst acidity. Catalyst regeneration for any of the specified catalysts is typically carried out using procedures which limit the maximum temperature to which the catalyst is exposed during regeneration to about 750° C., more typically to about 650° C. Conventional catalyst regeneration methods can be used, e.g., exposing the catalyst to an oxidant such as air or oxygen in air for a time sufficient to remove at least a portion of the catalyst coke, but the invention is not limited thereto. When stages 1 and/or 3 are carried out in a set of fixed-bed, adiabatic reactors in series, a suitable regeneration procedure includes circulating a stream of regeneration gas containing a limited amounts of oxygen, which limits the size of the exotherm where coke is burned off the catalyst. Typically, at the location where the regeneration gas enters the first (most upstream, with respect to the flow of regeneration gas) reactor, e.g., at the reactor's inlet, the regeneration gas is exposed to a temperature ≤350° C., e.g., ≤325° C., such as ≤300° C. If needed, the oxidant content of the regenerating gas can be decreased to lessen the risk of exceeding the maximum temperature.

In certain aspects, the dehydrocyclization catalyst of the first and/or third stage have a residence time of ≤90 seconds in the dehydrocyclization reaction zone under dehydrocyclization conditions. It has been discovered that doing so dramatically increases the conversion of $C_{2+}$ hydrocarbon without a significant decrease in the selectivity for aromatic hydrocarbon, and without excessive selectivity for light hydrocarbon compounds such as methane. More particularly, it has been found that it is beneficial for the dehydrocyclization catalyst to have a residence time in the reaction of stage 1 and/or stage 3 under the specified dehydrocyclization conditions of ≤60 seconds, e.g., ≤30 seconds, such as ≤10 seconds, or ≤1 second, or ≤0.1 second or in the range of from 0.001 second to 60 seconds. Especially when the catalyst is present in a moving bed and/or fluidized bed, it is beneficial for the dehydrocyclization catalyst to have a residence time in the dehydrocyclization reaction zone that is in the range of from 0.01 second to 1 second. After the specified residence time, the dehydrocyclization catalyst is typically at least partially regenerated and then returned to dehydrocyclization service. The regeneration can be carried out in the reaction zone. Alternatively or in addition, the dehydrocyclization catalyst can be removed from the reaction zone after the specified residence time, at least partially regenerated outside of the reaction zone, and then returned to the reaction zone for continued dehydrocyclization after the regeneration.

A second product is produced by reacting the specified raffinate with the specified catalyst under the specified conditions in reaction zone 190. The second product is conducted away via line 200. Generally, the second product comprises (i) ≥0.5 wt. % of additional aromatic hydrocarbon, (ii) additional molecular hydrogen, and (iii) an amount $A_4$ wt. % of ethane; wherein $A_4 < A_3$, and $(A_4/A_3) < (A_2/A_1)$. Operating stage 3 under the specified conditions with the specified catalyst typically results in converting ≥5 wt. % of the ethane present in the raffinate, e.g., ≥10 wt. %, such as ≥20 wt. %. Contrary to expectations, it has been found that the conversion of any $C_4$ and/or $C_3$ hydrocarbon in the raffinate is generally less than the conversion of those compounds achieved in stage 1, even though $T_2$ exceeds $T_1$. Since the first product and raffinate typically contain ≤5 wt. % of $C_{3+}$ hydrocarbon, e.g., ≤2 wt. % propane, and ≤1 wt. % butanes, it is typical for little if any conversion of $C_{3+}$ hydrocarbon to occur in zone 190. This effect desirably decreases the accumulation of catalyst coke in stage 3.

As a result of the selective conversion of the raffinate's ethane, the amount of ethane (wt. basis) in the second product is typically less than that of the raffinate, e.g., $A_4 < 0.90 \cdot A_3$, such as $A_4 < 0.75 \cdot A_3$, or $A_4 < 0.5 \cdot A_3$. Operating reaction stage 3 under the specified conditions with the specified catalyst typically results in a greater amount of ethane conversion than occurs in stage 1, e.g., $(A_4/A_3) \leq 0.90 \cdot (A_2/A_1)$, such as $(A_4/A_3) \leq 0.75 \cdot (A_2/A_1)$, or $(A_4/A_3) \leq 0.5 \cdot (A_2/A_1)$. In particular aspects, $T_1 \leq 0.90 \cdot T_2$, $A_4 < 0.95 \cdot A_3$ and $(A_4/A_3) \leq 0.95 \cdot (A_2/A_1)$.

The aromatic hydrocarbon (and molecular hydrogen) of the second product are "additional" in the sense that they are in addition to those produced in stage 1, without regard to whether they are actually combined with those produced in stage 1. The second product typically comprises ≥1 wt. % of additional aromatic hydrocarbon, based on the weight of the second product, e.g., ≥2 wt. %, such as ≥10 wt. %, or ≥25 wt. %, or ≥50 wt. %, or ≥75 wt. %, or ≥90 wt. %. The process produces a desirable BTX product, particularly when the extract's aromatic hydrocarbon is combined with the second product's aromatic hydrocarbon. The aromatics separation of the second stage has been found to increase total aromatic hydrocarbon yield in the third stage. Even though $T_2$ is greater than $T_1$, it has been found that the second product has an unexpected increase in desirable xylene isomers, and an unexpected decrease yield of less desirable $C_{11+}$ aromatic hydrocarbon.

In certain aspects ≥90 wt. % of the additional aromatic hydrocarbon is separated from the second product, and at least a portion of the separated additional aromatic hydrocarbon is combined with at least a portion of the extract's aromatic hydrocarbon. Light hydrocarbon, e.g., ethane, can be present in the second product. Methane, when present in the feed, does not typically convert to other hydrocarbon compounds under the conditions specified for stage 1 and/or stage 3; consequently substantially all of the feed methane typically is present in the second product. The second product will also typically include additional methane, namely that produced in stages 1 and 3, e.g., by hydrogenolysis of $C_{2+}$ hydrocarbon. The second product's methane can be recovered, and at least a portion of the recovered methane can be utilized for operating one or more of (i) fired heaters for heat transfers 112 and/or 170, (ii) electric power generation, e.g., when electric heating is used to provide at least a portion of the heat needed for sustaining the endothermic dehydrocyclization reactions of one or more of zones 110, 120, and 190, and (iii) recycle to line 100 for use as feed diluent. When ethane is present in the second product, a first portion of the second product's ethane typically is unreacted feed ethane, with a second portion typically being additional ethane produced in stage 1 and/or stage 3. At least a portion of the second product's ethane (and any other light hydrocarbon), can be recovered and recycled to line 100, for example. It has been found that the total selectivity for one or more of (i) additional methane, (ii) additional ethane, and (iii) additional $C_{3+}$ light hydrocarbon in stages 1 and 3 is unexpectedly less than would be the case if stages 1 and 3 were combined into a single stage located upstream of stage 2 and operating under conditions specified for either stage 1 or stage 3. Typically, for a feed comprising natural gas, e.g., raw natural gas, such as Associated Gas, the process (e.g., stage 1, 2, and 3 operating together) exhibits (i) a total conversion of $C_2$-$C_4$ hydrocarbon ≥30%, e.g., ≥40%, such as ≥50%, and (ii) a selectivity for aromatic hydrocarbon ≥30%, e.g., ≥40%, such as ≥50%. Desirably, this performance can be achieved in a single pass.

Although the catalyst used in reaction zone 190 can be the substantially the same as that used in reaction zone 110 (and/or in optional reaction zone 120), typically the catalysts are different. For example, in certain aspects utilizing a feed comprising raw natural gas (<0.01 wt. % aromatic hydrocarbon), e.g., Associated Gas:

(i) The catalyst of reaction zone 110, and of optional reaction zone 120 when used, (Catalyst A, a particular form of the first catalyst) is located in at least one fixed bed and comprises a molecular sieve component, a dehydrogenation component, and optionally a matrix component. The molecular sieve component comprises ≥90 wt. % of a aluminosilicate in hydrogen form, the aluminosilicate having a constraint index in the range of from 2-12 (e.g., phosphorous-modified H-ZSM-5) and a silica to alumina ratio in the range of from 50 to 80. The molecular sieve component can comprises ≥95 wt. % of substantially binder-free, small crystal H-ZSM-5. The dehydrogenation component comprises ≥90 wt. % of at least one oxide of Ga. The matrix component comprises ≥75 wt. % of alumina, silica, and combinations thereof. The catalyst optionally comprises ≥1 wt. % phosphorus, e.g., in the form of phosphorous-modified H-ZSM-5 and/or by including phosphorous in the matrix component (ii) The catalyst of reaction zone 190 (Catalyst B, a particular form of the second catalyst) is located in at least one fixed bed and comprises a molecular sieve component, a dehydrogenation component, and optionally a matrix component. The molecular sieve component comprises ≥90 wt. % of an aluminosilicate in hydrogen form, the aluminosilicate having a constraint index in the range of from 2-12 (e.g., small crystal H-ZSM-5) and a silica to alumina ratio in the range of from 3 to 60, e.g., from 10 to 40, such as from 15 to 35. The dehydrogenation component comprises ≥90 wt. % of at least one oxide of Zn. The matrix component when used comprises ≥90 wt. % of alumina, silica, and combinations thereof. Catalyst B typically comprises <0.01 wt. % phosphorus.

Although Catalyst A and Catalyst B are each typically located in a plurality of fixed beds, optionally with heat added to the process at one or more locations between at least two of the fixed catalyst beds, other forms of catalyst beds can be used such as moving beds and/or fluidized beds. The feed reacts in the presence of Catalyst A in reaction zone 110 while exposed to a temperature $T_1$ in the range of from 450° C. to 605° C. and a pressure $P_1$ in the range of from 37 psia (255.1 kPa) to 100 psia (689.5 kPa), at a space velocity (WHSV) in the range of from 0.1 hr$^{-1}$ to 20 hr$^{-1}$, such as from 0.25 hr$^{-1}$ to 2 hr$^{-1}$. Typically, the raffinate comprises substantially the entire non-solid, non-aromatic portion of the first product. The raffinate reacts in the presence of Catalyst B in reaction zone 190 while exposed to a temperature $T_2$ in the range of from 500° C. to 675° C. and a pressure $P_2 \leq 32$ psia (220.6 kPa), at a space velocity (WHSV) in the range of from 0.1 hr$^{-1}$ to 20 hr$^{-1}$, such as from 0.25 hr$^{-1}$ to 2 hr$^{-1}$, and typically less than the WHSV used when reacting the feed in the presence of catalyst A. More particularly, $T_1 \leq 0.90 \cdot T_2$ and $P_2 \leq 0.90 \cdot P_1$, with $P_2$ in the range of 1 psia to 32 psia (220.6 kPa), e.g., 5 psia (34.5 kPa) to 30 psia (206.8 kPa), or 5 psia (34.5 kPa) to 29 psia (199.9 kPa).

Example 1

A representative raffinate comprising 50 mole % methane, 25 mole % ethane, and 25 mole % molecular hydrogen is reacted under stage 3 conditions which include a temperature of 600° C. in the presence of a representative stage 3 dehydrocyclization catalyst comprising ZSM-5 and 0.5 wt. % zinc under reaction conditions 1A-1D as tabulated in Table 2. Tabulated analyses of reaction products are also included in Table 2.

TABLE 2

| Reaction | 1A | 1B | 1C | 1D |
| --- | --- | --- | --- | --- |
| WHSV (hr$^{-1}$) | 0.257 | 0.263 | 0.263 | 0.257 |
| Pressure (kPa) | 200 | 200 | 250 | 250 |
| C$_1$ Conversion (%) | −31.4 | −34.0 | −23.2 | −25.3 |
| C$_2$ Conversion (%) | 46.0 | 43.3 | 25.9 | 26.4 |
| Reaction Product Hydrocarbon Content (wt. %) | | | | |
| Methane | 71.3 | 77.5 | 74.5 | 73.5 |
| Ethane | 0.0 | 0.0 | 0.0 | 0.0 |
| Ethylene | 7.1 | 4.5 | 8.5 | 8.5 |
| Propane | 0.3 | 0.3 | 1.2 | 1.1 |
| Propylene | 0.0 | 0.0 | 0.4 | 0.4 |

TABLE 2-continued

| Reaction | 1A | 1B | 1C | 1D |
| --- | --- | --- | --- | --- |
| C$_{6+}$ hydrocarbon | 21.3 | 17.6 | 15.3 | 16.5 |
| Benzene | 8.4 | 8.0 | 7.2 | 7.8 |
| Toluene | 5.3 | 4.9 | 4.3 | 4.6 |
| C$_8$ Aromatics | 0.9 | 0.7 | 0.7 | 0.8 |
| C$_{6+}$ non-aromatics | 6.6 | 4.0 | 3.0 | 3.3 |
| Methane yield (%) | 67.4 | 67.9 | 61.3 | 61.5 |
| Ethane yield (%) | 26.1 | 27.1 | 34.8 | 34.1 |
| Ethylene yield (%) | 1.6 | 1.0 | 1.3 | 1.4 |
| Propane yield (%) | 0.1 | 0.1 | 0.2 | 0.2 |
| Propylene yield (%) | 0.0 | 0.0 | 0.1 | 0.1 |
| Toluene yield (%) | 1.2 | 1.1 | 0.7 | 0.8 |
| Benzene yield (%) | 1.9 | 1.8 | 1.1 | 1.3 |
| C$_8$ Aromatics yield (%) | 0.2 | 0.2 | 0.1 | 0.1 |
| C$_{6+}$ Hydrocarbon Yield (%), total-including Aromatics | 4.8 | 3.9 | 2.4 | 2.8 |
| Aromatics Yield (%) | 3.3 | 3 | 1.9 | 2.2 |

The results of reactions 1A-1D demonstrate the benefit of operating stage 3 at a pressure $P_2 \leq 35$ psia (241.3 kPa). Operating at a pressure $P_2 > 36$ psia (248 kPa) as in reactions 1C and 1D results in a significant decrease in the yield of aromatic hydrocarbon, and an even more significant decrease in total C$_{6+}$ hydrocarbon yield. The results also show an undesirable increase in WHSV sensitivity at increased pressure.

Example 2

Figure 3:
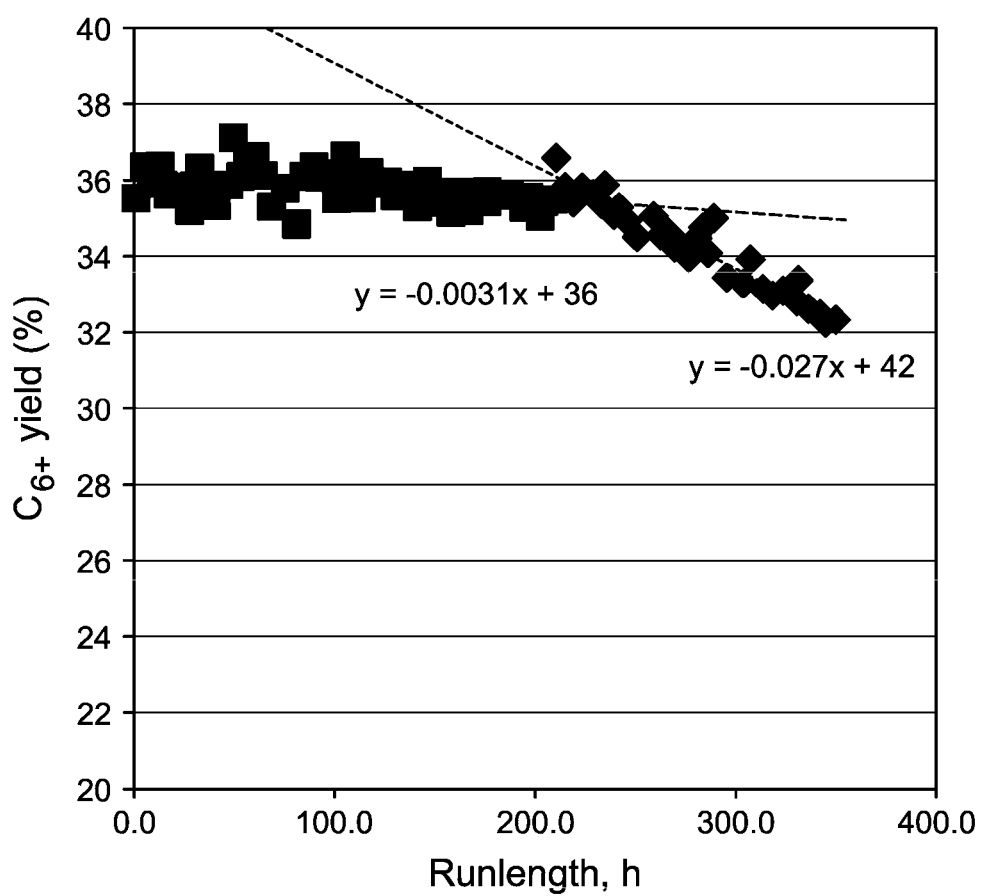
FIG. 3 shows the variation of $C_{6+}$ hydrocarbon yield (%) as a function of run-length (hours) from start of run, when the stage 1 dehydrocyclization reaction is carried out with a representative feed in the presence of a representative catalyst. The data corresponds to pressure of 400 kPa (solid rectangles) and 200 kPa (solid diamonds).

A representative feed comprising 35 wt. % methane, 18 wt. % ethane, 24 wt. % propane, and 23 wt. % butanes is reacted in the presence of a representative stage 1 dehydrocyclization catalyst comprising ZSM-5 and 1.5 wt. % gallium. The reaction is carried out under representative stage 1 dehydrocyclization conditions which include a WHSV of about 0.9 hr$^{-1}$ and a pressure of 400 kPa. As shown in FIG. 3, the yield of C$_{6+}$ hydrocarbon (including aromatic hydrocarbon) is substantially constant for a time duration of 200 hours from the start of the reaction. After 200 hours the pressure is decreased to 200 kPa, with the feed and other process conditions substantially constant, resulting in a very slow rate of catalyst deactivation (e.g., from catalyst coking), as evidenced by the substantially constant yield of C$_{6+}$ hydrocarbon. As shown in FIG. 3, the pressure change results in a substantial increase in the catalyst deactivation rate. Following an initial increase, the yield of C$_{6+}$ hydrocarbon rapidly decreases after about 210 hours until the reaction is halted at 350 hours. This example shows the benefit of operating stage 1 at greater pressure than stage 3.

Example 3

A representative feed comprising 35 wt. % methane, 18 wt. % ethane, 24 wt. % propane, and 23 wt. % butanes is reacted in the presence of a representative stage 1 dehydrocyclization catalyst comprising ZSM-5 and 1.5 wt. % gallium. The reaction is carried out for a duration of 72 hours under representative stage 1 process conditions tabulated in Table 3.

TABLE 3

| Reaction | 3A | 3B | 3C |
| --- | --- | --- | --- |
| Temperature (° C.) | 550 | 575 | 600 |
| WHSV (hr$^{-1}$) | 0.9 | 0.8 | 0.8 |
| Pressure (kPa) | 400 | 400 | 400 |

TABLE 3-continued

| Reaction | 3A | 3B | 3C |
|---|---|---|---|
| Initial $X_{1P}$ (%) | 64.6 | 80.7 | 87.2 |
| Final $X_{1P}$ (%) | 41.2 | 24.8 | 33.5 |
| Initial $X_{1B}$ (%) | 99.2 | 99.7 | 99.8 |
| Final $X_{1B}$ (%) | 95.4 | 78.5 | 70.5 |
| Initial $C_{6+}$ Yield | 32.8 | 33.5 | 34.9 |
| Final $C_{6+}$ Yield | 25.6 | 18.9 | 14.4 |

As shown in Table 3, $X_{MP}$ and $X_{MB}$ occur at a reaction temperature greater than 600° C. $X_{MP}$ is estimated to occur at approximately 650° C. for the feed, catalyst, and process conditions of this example. $X_{MB}$ is estimated to occur closer to 600° C. Although the initial $C_{6+}$ hydrocarbon yield is slightly greater at a temperature 600° C., the final yield of $C_{6+}$ hydrocarbon is significantly less. It is believed that this significant yield decrease primarily results from an increased catalyst deactivation rate. Although lesser values of the initial $C_{6+}$ hydrocarbon yield are observed at 575° C. and 550° C., rate of catalyst deactivation is more than proportionately diminished, leading to a greater final yield of $C_{6+}$ hydrocarbon and a greater total amount of aromatic hydrocarbon produced during the 72 hour run time. Accordingly, this example shows the benefit of operating stage 1 at an $X_{1P}<X_{MP}$ and $X_{1B}<X_{MB}$.

All patents, test procedures, and other documents cited herein, including priority documents, are fully incorporated by reference to the extent such disclosure is not inconsistent and for all jurisdictions in which such incorporation is permitted.

While the illustrative forms disclosed herein have been described with particularity, it will be understood that various other modifications will be apparent to and can be readily made by those skilled in the art without departing from the spirit and scope of the disclosure. Accordingly, it is not intended that the scope of the claims appended hereto be limited to the examples and descriptions set forth herein but rather that the claims be construed as encompassing all the features of patentable novelty which reside herein, including all features which would be treated as equivalents thereof by those skilled in the art to which this disclosure pertains.

When numerical lower limits and numerical upper limits are listed herein, ranges from any lower limit to any upper limit are contemplated, and are expressly within the scope of the invention. The term "comprising" is synonymous with the term "including". Likewise whenever a composition, an element or a group of components is preceded with the transitional phrase "comprising", it is understood that we also contemplate the same composition or group of components with transitional phrases "consisting essentially of", "consisting of", "selected from the group consisting of", or "is" preceding the recitation of the composition, component, or components, and vice versa.

The invention claimed is:

1. A hydrocarbon conversion process, comprising:
   (a) providing a feed comprising $A_1$ wt. % ethane, $A_1$ being at least 1, and at least 1 wt. % of $C_{3+}$ paraffinic hydrocarbon;
   (b) providing first and second catalysts, wherein (i) the first catalyst comprises at least 10 wt. % of a first molecular sieve component and at least 0.005 wt. % of a first dehydrogenation component and (ii) the second catalyst comprises at least 10 wt. % of a second molecular sieve component and at least 0.005 wt. % of a second dehydrogenation component;
   (c) contacting the feed with the first catalyst under catalytic dehydrocyclization conditions, including a temperature $T_1$ in the range of from 400° C. to 630° C. and a pressure $P_1$ greater than 35 psia (241.3 kPa), to produce a first product comprising (i) at least 1 wt. % of aromatic hydrocarbon, (ii) molecular hydrogen, (iii) $A_2$ wt. % ethane, $A_2$ being at least $0.75 \cdot A_1$;
   (d) producing a raffinate by removing from the first product an extract comprising at least 50 wt. % of the first product's aromatic hydrocarbon, wherein the raffinate comprises ethane in an amount $A_3$ wt. %, $A_3$ being greater than $A_2$; and
   (e) contacting at least a portion of the raffinate with the second catalyst under catalytic dehydrocyclization conditions, including a temperature $T_2$ in the range of from 450° C. to 700° C., and a pressure $P_2 \leq 35$ psia (241.3 kPa), to produce a second product comprising at least 0.5 wt. % of additional aromatic hydrocarbon and ethane in an amount $A_4$ wt. %, wherein $T_1$ does not exceed $0.90 \cdot T_2$, $P_2$ is less than $P_1$, $A_4$ is less than $A_3$, and $(A_4/A_3)$ is less than $(A_2/A_1)$.

2. The process of claim 1, wherein (i) the first and second molecular sieve components each comprise (i) one or more of MCM-22, ZSM-5, ZSM-11, ZSM-12, ZSM-22, ZSM-23, ZSM-35, and ZSM-48 and/or (ii) the first and second dehydrogenation components each comprise one or more of Ga, Zn, Cu, Re, Mo, W, La, Fe, Ag, Pt, and Pd.

3. The process of claim 1, wherein the first and second catalysts have substantially the same composition.

4. The process of claim 1, wherein
   (i) the catalytic dehydrocyclization conditions of step (c) include one or more of $T_1$ in the range of from 450° C. to 605° C., $P_1$ in the range of from 37 psia (255.1 kPa) to 80 psia (522 kPa), and a space velocity (WHSV) in the range of from 0.1 hr$^{-1}$ to 20 hr$^{-1}$, and the catalytic dehydrocyclization conditions of step (e) include one or more of $T_2$ in the range of from 500° C. to 675° C., $P_2 \leq 30$ psia (207 kPa), and a space velocity (WHSV) in the range of from 0.1 hr$^{-1}$ to 20 hr$^{-1}$.

5. The process of claim 1, wherein
   (i) $A_1$ is in the range of from 10 to 40, and the feed further comprises methane, propane, and butanes;
   (ii) $A_2$ is greater than or equal to $A_1$;
   (iii) $A_4$ is less than $0.90 \cdot A_3$; and
   (iv) $(A_4/A_3)$ does not exceed $0.90 \cdot (A_2/A_1)$.

6. The process of claim 1, wherein
   (i) the feed comprises 1 wt. % to 40 wt. % methane; $A_1$ wt. % ethane, $A_1$ being in the range of from 10 wt. % to 40 wt. %; 20 wt. % to 50 wt. % propane; and 20 wt. % to 50 wt. % butanes; and substantially saturated $C_{5+}$ hydrocarbon;
   (ii) $A_2$ is at least 10, the first product comprises at least 5 wt. % aromatic hydrocarbon and at least 1 wt. % molecular hydrogen, and the first product further comprises at least 10 wt. % methane, no more than 2 wt. % propane, and no more than 1 wt. % butanes;
   (iii) the raffinate comprises at least 10 wt. % of the first product's molecular hydrogen, at least 10 wt. % of the first product's methane, and at least 95 wt. % of the first product's ethane; but no more than 5 wt. % of the first product's aromatic hydrocarbon;
   (iv) $A_4$ does not exceed $0.75 \cdot A_3$, and the second product comprises at least 2 wt. % of the additional aromatic hydrocarbon;
   (v) $(A_4/A_3)$ does not exceed $0.75 \cdot (A_2/A_1)$; and
   (vi) $P_2$ does not exceed $0.80 \cdot P_1$.

7. The process of claim 1, further comprising (i) separating from the second product ≥90 wt. % of the additional aromatic hydrocarbon and (ii) combining at least a portion of the separated additional aromatic hydrocarbon with at least a portion of the extract's aromatic hydrocarbon.

8. The process of claim 1, wherein raffinate includes at least 25 wt. % of the first product's molecular hydrogen.

9. The process of claim 1, wherein at least 90 wt. % of the first catalyst is located in a first fixed catalyst bed and at least 90 wt. % of the second catalyst is located in a second fixed catalyst bed.

10. The process of claim 1, wherein (i) the catalytic dehydrocyclization conditions of step (e) encompass a maximum ethane conversion to aromatic hydrocarbon $X_{ME}$, (ii) during step (e) the raffinate's ethane is converted to aromatic hydrocarbon at a conversion $X_3$, (iii) $X_3$ does not exceed $0.90 \cdot X_{ME}$, and (iv) step (e) is carried out for an average cycle time of at least 120 hours.

11. A hydrocarbon upgrading process, comprising:
(a) providing a feed comprising $A_1$ wt. % ethane, $A_1$ being at least 10; 1 wt. % to 40 wt. % methane; 20 wt. % to 50 wt. % propane; and 20 to 50 wt. % butanes;
(b) providing first and second catalysts, wherein (i) the first catalyst comprises ≥25 wt. % of a first molecular sieve component and ≥0.5 wt. % of a first dehydrogenation component and (ii) the second catalyst comprises ≥25 wt. % of a second molecular sieve component and ≥0.5 wt. % of a second dehydrogenation component;
(c) contacting the feed with the first catalyst under catalytic dehydrocyclization conditions, including a temperature $T_1$ in the range of from 400° C. to 630° C. and a pressure $P_1$ greater than 35 psia (241.3 kPa), to produce a first product comprising ≥10 wt. % aromatic hydrocarbon; molecular hydrogen; $A_2$ wt. % ethane, $A_2$ being greater than or equal to $A_1$; 1 wt. % to 40 wt. % methane; ≤1 wt. % propane, and ≤1 wt. % butanes;
(d) producing a raffinate by removing from the first product an extract comprising ≥90 wt. % of the first product's aromatic hydrocarbon, wherein (i) the raffinate comprises $A_3$ wt. % ethane and (ii) $A_3$ is at least $1.25 \cdot A_2$; and
(e) contacting at least a portion of the raffinate with the second catalyst under catalytic dehydrocyclization conditions, including a temperature $T_2$ in the range of from 450° C. to 700° C., and a pressure $P_2$ that does not exceed 35 psia (241.3 kPa), to produce a second product comprising at least 0.5 wt. % of additional aromatic hydrocarbon and an amount $A_4$ wt. % of ethane; wherein $T_1$ does not exceed $0.90 \cdot T_2$, $P_2$ is less than $P_1$, $A_4$ does not exceed $0.95 \cdot A_3$, and $(A_4/A_3)$ does not exceed $0.95 \cdot (A_2/A_1)$.

12. The process of claim 11, wherein (i) the first catalyst comprises at least 90 wt. % of the first molecular sieve component; the second catalyst comprises at least 90 wt. % of the second molecular sieve component; the first and second molecular sieve components each comprise one or more of MCM-22, ZSM-5, ZSM-11, ZSM-12, ZSM-22, ZSM-23, ZSM-35, and ZSM-48; the first catalyst comprises at least 1 wt. % the first dehydrogenation component; the second catalyst comprises at least 1 wt. % the second dehydrogenation component; and the first and second dehydrogenation components each comprise two or more of Ga, Zn, Cu, Re, Mo, W, La, Fe, Ag, Pt, and Pd.

13. The process of claim 11, wherein (i) the first catalyst comprises at least 50 wt. % of the first molecular sieve component and at least 1 wt. % of the first dehydrogenation component; (ii) the first molecular sieve component comprises at least 90 wt. % of (A) ZSM-5 and/or (B) ZSM-12; and (iii) the first dehydrogenation component comprises ≥90 wt. % of (A) Ga and/or (B) Zn.

14. The process of claim 11, wherein
(i) the catalytic dehydrocyclization conditions of step (c) include one or more of include one or more of $T_1$ in the range of from 450° C. to 605° C., $P_1$ in the range of from 37 psia (255.1 kPa) to 80 psia (522 kPa), and a space velocity (WHSV) in the range of from 0.1 hr$^{-1}$ to 20 hr$^{-1}$;
(ii) the catalytic dehydrocyclization conditions of step (e) include one or more of $T_2$ in the range of from 500° C. to 675° C., $P_2 \leq 30$ psia (207 kPa), and a space velocity (WHSV) in the range of from 0.1 hr$^{-1}$ to 20 hr$^{-1}$;
(iii) the first dehydrogenation component comprises at least 95 wt. % Ga;
(iv) the first molecular sieve component comprises at least 90 wt. % of aluminosilicate having a silica:alumina ratio in the range of from 50 to 80;
(v) the second dehydrogenation component comprises at least 95 wt. % Zn; and
(vi) the second molecular sieve component comprises at least 90 wt. % of aluminosilicate having a silica:alumina ratio in the range of from 10 to 40.

15. The process of claim 11, wherein
(i) the feed is derived from unfractionated natural gas;
(ii) the first product comprises at least 25 wt. % aromatic hydrocarbon, at least 2 wt. % molecular hydrogen, at least 10 wt. % methane, no more than 2 wt. % propane, no more than 1 wt. % butanes, and $A_2$ wt. % ethane, $A_2$ being at least 20;
(iii) the raffinate comprises at least 10 wt. % of the first product's molecular hydrogen, at least 10 wt. % of the first product's methane, and at least 95 wt. % of the first product's ethane; but no more than 1 wt. % of the first product's aromatic hydrocarbon;
(iv) $A_4$ does not exceed $0.75 \cdot A_3$, and the second product comprises at least 1 wt. % of the additional aromatic hydrocarbon;
(v) $(A_4/A_3)$ does not exceed $0.75 \cdot (A_2/A_1)$; and
(vi) $P_2$ does not exceed $0.80 \cdot P_1$.

16. The process of claim 11, wherein raffinate contains at least 95 wt. % of the first product's methane and/or at least 95 wt. % of the first product's molecular hydrogen.

17. The process of claim 11, further comprising producing a second raffinate by removing from the second product an extract comprising ≥90 wt. % of any of the aromatic hydrocarbon in the second product and at least 90 wt. % of the additional aromatic hydrocarbon, wherein
(i) the second raffinate comprises no more than 12 wt. % ethane, no more than 5 wt. % propane, no more than 2 wt. % butanes, and at least 95 wt. % the balance of the raffinate comprises methane;
(ii) the second raffinate has a Wobbe Index in the range of from 49.01 MJ/sm$^3$ to 52.22 MJ/sm$^3$ and has heating value in the range of from 36.07 MJ/sm$^3$ to 41.40 MJ/sm$^3$, and
(iii) the process does not include cryogenic methane separation before step (a).

18. The process of claim 11, wherein (i) at least 90 wt. % of the first catalyst is located in at least a first fixed catalyst bed, (ii) at least 90 wt. % of the second catalyst is located in at least a second fixed catalyst bed, (iii) the catalytic dehydrocyclization conditions of step (e) encompass a maximum ethane conversion to aromatic hydrocarbon $X_{ME}$, (iv) during step (e) the raffinate's ethane is converted to aromatic hydrocarbon at a conversion $X_{3E}$, (v) $X_{3E}$ does not exceed $0.90 \cdot X_{ME}$, and (vi) step (e) is carried out for an average cycle time ≥120 hours.

19. The process of claim 11, wherein the first and second catalysts have substantially the same composition.

20. The process of claim 18, wherein (i) the catalytic dehydrocyclization conditions of step (c) encompass a maximum propane conversion to aromatic hydrocarbon $X_{MP}$, (iv) during step (c) the feed's propane is converted to aromatic hydrocarbon at a conversion $X_{1P}$, (v) $X_{1P}$ does not exceed $0.90 \cdot X_{MP}$, and (vi) step (c) is carried out for an average cycle time of at least 120 hours.

21. A process for upgrading paraffinic hydrocarbon, comprising:
   (a) providing a feed comprising $A_1$ wt. % ethane, $A_1$ being less than 1; no more than 1 wt. % of aromatic hydrocarbon; and at least 1 wt. % of $C_{3+}$ paraffinic hydrocarbon;
   (b) providing first and second catalysts, wherein (i) the first catalyst comprises at least 25 wt. % of a first molecular sieve component and at least 0.5 wt. % of a first dehydrogenation component and (ii) the second catalyst comprises at least 25 wt. % of a second molecular sieve component and at least 0.5 wt. % of a second dehydrogenation component;
   (c) contacting the feed with the first catalyst under catalytic dehydrocyclization conditions, including a temperature $T_1$ in the range of from 400° C. to 630° C. and a pressure $P_1$ greater than 35 psia (241.3 kPa), to produce a first product comprising at least 10 wt. % aromatic hydrocarbon; molecular hydrogen; an amount $A_2$ of ethane, $A_2$ being at least 1; 1 wt. % to 40 wt. % methane; no more than 2 wt. % propane; and no more than 1 wt. % butanes;
   (d) producing a raffinate by removing from the first product an extract comprising ≥90 wt. % of the first product's aromatic hydrocarbon, wherein the raffinate comprises $A_3$ wt. % ethane, $A_3$ being at least $1.25 \cdot A_2$; and
   (e) contacting at least a portion of the raffinate with the second catalyst under catalytic dehydrocyclization conditions, including a temperature $T_2$ in the range of from 450° C. to 700° C., and a pressure $P_2$ that does not exceed 35 psia (241.3 kPa), to produce a second product comprising at least 1 wt. % of additional aromatic hydrocarbon and an amount $A_4$ wt. % of ethane; wherein $T_1$ does not exceed $0.90 \cdot T_2$, $P_2$ is less than $P_1$, and $A_4$ does not exceed $0.95 \cdot A_3$.

22. The process of claim 21, wherein
   (i) the catalytic dehydrocyclization conditions of step (c) include one or more of $T_1$ in the range of from 450° C. to 605° C., $P_1$ in the range of from 37 psia (255.1 kPa) to 80 psia (522 kPa), and a space velocity (WHSV) in the range of from 0.1 hr$^{-1}$ to 20 hr$^{-1}$, and
   (ii) the catalytic dehydrocyclization conditions of step (e) include one or more of $T_2$ in the range of from 500° C. to 675° C., $P_2 \leq 30$ psia (207 kPa), and a space velocity (WHSV) in the range of from 0.1 hr$^{-1}$ to 20 hr$^{-1}$.

23. The process of claim 21, wherein
   (i) $A_1$ does not exceed 0.1 and $A_2 \geq 10$;
   (ii) the first product comprises at least 25 wt. % aromatic hydrocarbon, at least 2 wt. % molecular hydrogen, at least 10 wt. % methane, no more than 2 wt. % propane, and no more than 1 wt. % butanes;
   (iii) the raffinate comprises at least 95 wt. % of the first product's molecular hydrogen, at least 95 wt. % of the first product's methane, at least 95 wt. % of the first product's ethane; but no more than 1 wt. % of the first product's aromatic hydrocarbon;
   (iv) $A_4$ does not exceed $0.75 \cdot A_3$, and the second product comprises at least 2 wt. % of the additional aromatic hydrocarbon; and
   (v) $(A_4/A_3)$ does not exceed $0.75 \cdot (A_2/A_1)$.

24. The process of claim 21, wherein
   (i) the first dehydrogenation component comprises at least 95 wt. % Ga;
   (ii) the first molecular sieve component comprises at least 95 wt. % of small crystal, substantially binder-free H-ZSM-5 and further comprises at least 1 wt, % phosphorous, and has a silica:alumina ratio in the range of from 50 to 80,
   (iii) the second dehydrogenation component comprises at least 95 wt. % Zn,
   (iv) the second molecular sieve component comprises at least 95 wt. % of small crystal H-ZSM-5 and has a silica:alumina ratio in the range of from 10 to 40; and
   (v) the first catalyst comprises no more than 1 wt. % of matrix.

25. A natural gas upgrading process, comprising:
   (a) providing a natural gas feed comprising methane and ≥13 wt. % ethane;
   (b) providing first and second catalysts, wherein (i) the first catalyst comprises ≥25 wt. % of a first molecular sieve component and ≥0.5 wt. % of a first dehydrogenation component and (ii) the second catalyst comprises ≥25 wt. % of a second molecular sieve component and ≥0.5 wt. % of a second dehydrogenation component;
   (c) contacting the feed with the first catalyst under catalytic dehydrocyclization conditions, including a temperature $T_1$ in the range of from 400° C. to 630° C. and a pressure $P_1$ greater than 35 psia (241.3 kPa), to produce a first product comprising ≥10 wt. % aromatic hydrocarbon; molecular hydrogen; $A_2$ wt. % ethane, wherein $A_2 \geq A_1$; methane; no more than 2 wt. % propane; and no more than 1 wt. % butanes;
   (d) producing a raffinate which comprises $A_3$ wt. % ethane by removing from the first product an extract comprising at least 90 wt. % of the first product's aromatic hydrocarbon, wherein (i) the raffinate further comprises ≥95 wt. % of the first product's molecular hydrogen and ≥95 wt. % of the first product's methane, and (ii) $A_3$ is at least $1.25 \cdot A_2$; and
   (e) contacting at least a portion of the raffinate with the second catalyst under catalytic dehydrocyclization conditions which encompass a maximum ethane conversion to aromatic hydrocarbon $X_{ME}$ and which include a temperature $T_2$ in the range of from 450° C. to 700° C. and a pressure $P_2$ that does not exceed 35 psia (241.3 kPa), to produce a second product comprising ≥2 wt. % of additional aromatic hydrocarbon and $A_4$ wt. % of ethane; wherein:
   (i) $T_1$ does not exceed $0.90 \cdot T_2$,
   (ii) $P_2$ does not exceed $0.90 \cdot P_1$,
   (iii) $A_4 < 0.95 \cdot A_3$,
   (iv) $(A_4/A_3)$ does not exceed $0.95 \cdot (A_2/A_1)$,
   (iv) the raffinate's ethane is converted to aromatic hydrocarbon at a conversion $X_3$, and
   (v) $X_3 \leq 0.90 \cdot X_{ME}$, and
   (f) producing a second raffinate by removing from the second product an extract comprising ≥90 wt. % of any of the aromatic hydrocarbon in the second product and ≥90 wt. % of the additional aromatic hydrocarbon, wherein (i) the second raffinate comprises no more than 12 wt. % ethane, no more than 5 wt. % propane, no more than 2 wt. % butanes, and at least 95 wt. % the balance of the raffinate comprises methane, (ii) the second raffinate has a Wobbe Index in the range of from 49.01 MJ/sm$^3$ to 52.22 MJ/sm$^3$ and has heating value in the range of from 36.07 MJ/sm$^3$ to 41.40 MJ/sm$^3$, and (iii) the process does not include cryogenic methane separation.

* * * * *